United States Patent
Austin

(10) Patent No.: US 7,722,663 B1
(45) Date of Patent: May 25, 2010

(54) ANATOMICALLY CORRECT ENDOLUMINAL PROSTHESES

(75) Inventor: Michael Stephen Austin, Galway (IE)

(73) Assignee: Scimed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 09/556,671

(22) Filed: Apr. 24, 2000

(51) Int. Cl.
*A61F 2/06* (2006.01)
(52) U.S. Cl. .................................................. 623/1.22
(58) Field of Classification Search ......... 623/1.1–1.54; 606/194
See application file for complete search history.

(56) References Cited

U.S. PATENT DOCUMENTS

| | | | | |
|---|---|---|---|---|
| 4,086,665 A | * | 5/1978 | Poirier | 623/1.44 |
| 4,410,126 A | | 10/1983 | O'Rourke | 228/180 |
| 4,553,545 A | * | 11/1985 | Maass et al. | 606/198 |
| 4,562,596 A | | 1/1986 | Kornberg | 623/1 |
| 4,577,631 A | | 3/1986 | Kreamer | 128/334 |
| 4,733,665 A | * | 3/1988 | Palmaz | 623/1.11 |
| 4,950,227 A | | 8/1990 | Savin et al. | 604/8 |
| 4,994,071 A | | 2/1991 | MacGregor | 606/194 |
| 5,019,090 A | * | 5/1991 | Pinchuk | 623/1.15 |
| 5,061,275 A | * | 10/1991 | Wallsten et al. | 623/1.22 |
| 5,104,404 A | * | 4/1992 | Wolff | 623/1.16 |
| 5,122,154 A | * | 6/1992 | Rhodes | 623/1.13 |
| 5,133,732 A | * | 7/1992 | Wiktor | 623/1.22 |
| 5,156,619 A | * | 10/1992 | Ehrenfeld | 623/1.31 |
| 5,356,433 A | * | 10/1994 | Rowland et al. | 424/422 |
| 5,387,235 A | | 2/1995 | Chuter | 623/1 |
| 5,405,377 A | * | 4/1995 | Cragg | 623/1.2 |
| 5,443,497 A | | 8/1995 | Venbrux | 623/1 |
| 5,484,444 A | | 1/1996 | Braunschweiler | 606/108 |
| 5,575,816 A | * | 11/1996 | Rudnick et al. | 623/1.15 |
| 5,609,625 A | | 3/1997 | Piplani et al. | 623/1 |
| 5,653,743 A | | 8/1997 | Martin | 623/1 |
| 5,693,086 A | | 12/1997 | Goicoechea et al. | 623/1 |
| 5,695,517 A | * | 12/1997 | Marin et al. | 623/1.15 |
| 5,709,713 A | | 1/1998 | Evans et al. | 623/1 |
| 5,843,120 A | * | 12/1998 | Israel et al. | 623/1.15 |
| 5,843,175 A | * | 12/1998 | Frantzen | 623/1.15 |
| 5,851,228 A | | 12/1998 | Pinheiro | 623/1 |
| 5,855,598 A | * | 1/1999 | Pinchuk | 623/1.13 |
| 5,893,887 A | | 4/1999 | Jayaraman | 623/1 |
| 6,027,525 A | * | 2/2000 | Suh et al. | 623/1.1 |
| 6,030,414 A | | 2/2000 | Taheri | 623/1 |
| 6,325,826 B1 | * | 12/2001 | Vardi et al. | 623/1.15 |

(Continued)

FOREIGN PATENT DOCUMENTS

FR 2 678 508 7/1991

(Continued)

*Primary Examiner*—Eduardo C Robert
*Assistant Examiner*—David Comstock
(74) *Attorney, Agent, or Firm*—Hoffman & Baron, LLP

(57) ABSTRACT

An anatomically correct endoluminal prosthesis is provided for placement in a lumen or vessel of a body. In a preferred embodiment, the prosthesis is a stent having at least one segment of curvature located along the body of the stent. The stent may have segments of curvature, apertures, tapers, flares, beveling, non-circular cross-sections, coverings or branching. Preferably, the stent has orientation markers and lines to allow for in vivo identification and orientation by conventional imaging formats. The stent may have multiple segments of curvature in succession or overlapping and may have segments of curvature lying in different planes of curvature. A method of forming the prosthesis is provided.

37 Claims, 21 Drawing Sheets

U.S. PATENT DOCUMENTS

| | | |
|---|---|---|
| 6,554,856 B1 | 4/2003 | Doorly |
| 2001/0049549 A1 | 12/2001 | Boylan |
| 2002/0019660 A1 | 2/2002 | Gianotti |

FOREIGN PATENT DOCUMENTS

| | | |
|---|---|---|
| JP | 9-164209 | 5/2001 |
| WO | WO 95/09585 | 4/1995 |
| WO | WO 98/53764 | 12/1998 |
| WO | WO 99/62430 | 12/1999 |
| WO | WO 01/30270 | 5/2001 |
| WO | WO 01/30270 A2 | 5/2001 |

\* cited by examiner

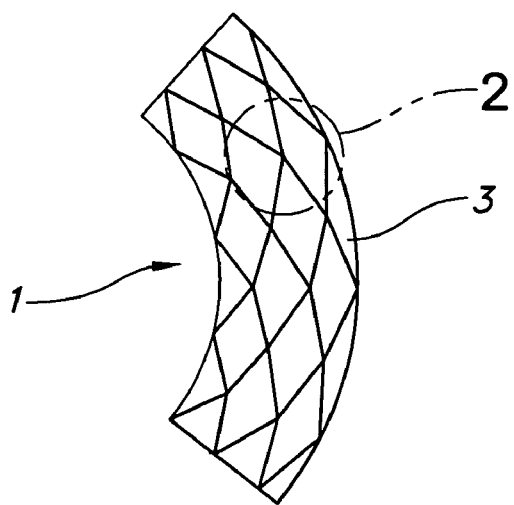
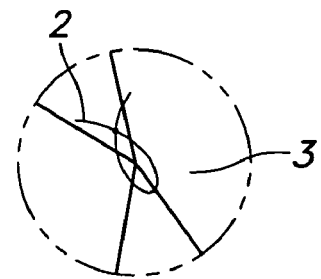
FIG. 1A
FIG. 1B
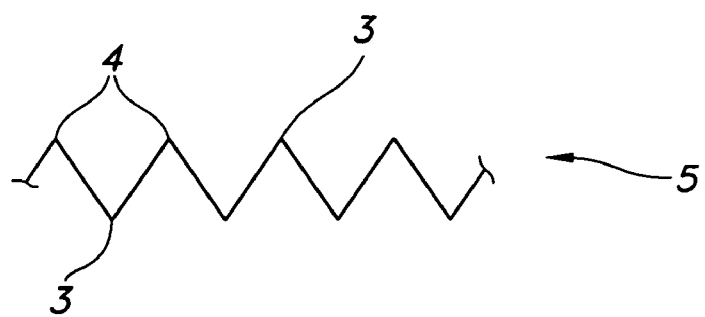
FIG. 2

ANATOMICALLY CORRECT ENDOLUMINAL PROSTHESES

BACKGROUND OF THE INVENTION

Stents are commonly used medical implants designed to prop open the inside of a patient's vessels or body lumens. In most cases, stents are used to treat occlusions that have formed within a body lumen such as a coronary artery or the biliary duct. The typical stent is a metal cylindrical tube that has been rendered flexible by its specific construction. A stent may be formed of a metal tube that has been etched or cut out to weaken the walls of the tube to such a point that the tube provides support to the body lumen in which it is placed, but offers enough flexibility so as to be deliverable on a catheter to the site in the body where it is deployed. As well, stents have been made by weaving or knitting metal wires to create a tube having good flexibility, sufficient radial strength and deliverability. Other stents have been made of polymers, biological materials, fabrics and combinations thereof.

In all cases, the stent must be designed such that it is deployable by catheter or similar stent delivery system, as it is desirable for stent placement procedures to be minimally invasive. By virtue of the openings in the wall of the stent, a stent may be reduced in radius when positioned on the delivery catheter. The stent may then be delivered through a small percutaneous opening in the body of the patient or through a natural orifice such as the mouth. In any event, low profile and controllability are necessities for delivering stents to body lumens. Once in position, a stent may be deployed by removing a constraint, such as a sheath, which has maintained low profile of the stent during delivery. Once the sheath is removed, the stent will self expand to support the vessel. Another common deployment method is to inflate a balloon inside the stent in order to force the stent open. The balloon is usually part of the delivery catheter, but it may be administered following an initial stent deployment by self-expansion or another balloon.

When deployed, stents will take their designed and manufactured shape which is, as stated above, a cylindrical tube. Stents can conform somewhat to the anatomy of the lumen in which it is deployed. As well, various designs and materials have been explored that allow the deployed stent to bend in place with the anatomy. Bending may occur in three dimensions. As a result of the straight cylindrical geometry of current stents, a patient's anatomy is induced to conform to the deployed stent shape rather than the stent conforming to the anatomical shape. A flexible material or design may relieve the influence of the stent on the vessel morphology, yet these factors cannot ideally suit a patient's anatomy.

The influence of a straight stent in a naturally curved lumen may reduce the advantages of relieving the occlusion in the lumen. In areas of fluid flow, as in the arterial tree, a transition from the artery's natural curvature to a straighter section supported by a stent may induce localized turbulence in the blood. Turbulence may itself lead to thrombosis or emboli formation, which can, in turn, occlude the vessel or vessels downstream. Additionally, a straight stent in a curved vessel will naturally exert higher stresses at the ends of the stent upon the lumen wall. Localized stresses may incite an injury response and potentially areas of increased restenosis. As well, the exertion of local stress on weakened vessels, as is often the case for patient's suffering from various diseases, may lead to complications such as erosion, abrasion or other types of injury on the sensitive cellular linings. Exposure of inner layers of a vessel in the vascular system will incite localized thrombus formation and possible emboli. Such injuries may also lead to vessel wall hyperplasia and possibly restenosis of the stented vessel. These factors are complicated by lumens that are submitted to pressure cycles, as in the arterial tree.

In addition to the influences of arterial pressure, surrounding tissues may have a marked influence on the intended effects of the stent. A stent in a coronary vessel is subjected to constant contractions and expansions of the heart. If the stent were imparting a straightening force upon the coronary artery, this force would be amplified at various points in the cardiac cycle. Another deleterious effect of surrounding tissue may be eventual stent migration. A stent that does not conform to the surrounding vessel may be induced to move along the axis of the vessel to an area of less longitudinal stress, especially during moments of surrounding tissue contraction. As might be expected, cardiac tissue is not the only type of contractile tissue. A stent located in a leg artery, vein or duct may be subjected to the surrounding forces of the leg muscles. In such a case, the effect of the patient's weight over an implanted stent may further exacerbate the stress between the vessel and the stent. Finally, stented lumens that are subjected to straightening from a tortuous natural state will suffer from a magnified effect of the stresses imposed on the lumen in both the axial and radial directions.

Further examples of body lumens that would benefit from an anatomically shaped stent include but are not limited to arteries, veins, cerebral vessels and lumens, biliary and pancreatic ducts, lymph ducts, the gastrointestinal or GI tract, the aorta, nasal passages, ear canals, tear ducts, the ureters, the intestines, reproductive organs and pulmonary tracts.

Other anatomical features that may be necessary to accommodate include vessel branching, tapering, flaring, non-round cross-sections and multiple curvatures. Each of these factors represents a non-straight tube anatomy that may be negatively affected by treatment with a simple straight tube stent.

As exemplified above, there exists a need to provide for stents that can be deployed by minimally invasive procedures wherein such stents are shaped to assume the geometry of the body lumen in which they are placed and further wherein the stents successfully support the lumen without the detrimental effects caused by imposing an unnatural shape upon a body lumen.

OBJECT OF THE INVENTION

It is an object of the present invention to provide for a medical implant for placement in a body lumen having at least one segment of curvature wherein at least a portion of the body of the medical implant is adapted to the size and shape of the body lumen.

It is a further object of the present invention to provide for an endoluminal prosthesis for placement in a body lumen having at least one segment of curvature wherein at least a portion of the body of endoluminal prosthesis is adapted to the size and shape of the body lumen.

Another object of the invention is to provide for an endoluminal prosthesis for placement in a body lumen having at least two segments of curvature in the same plane of curvature wherein at least a portion of the body of endoluminal prosthesis is adapted to the size and shape of the body lumen.

Another object of the invention is to provide for an endoluminal prosthesis for placement in a body lumen having at least two segments of curvature in different planes of curvature wherein at least a portion of the body of endoluminal prosthesis is adapted to the size and shape of the body lumen.

It is a further object of the invention is to provide for an endoluminal prosthesis for placement in a body lumen having at least two segments of curvature in different planes of curvature wherein at least a portion of the segments of curvature overlap and further wherein at least a portion of the body of endoluminal prosthesis is adapted to the size and shape of the body lumen.

It is a further object of the present invention to provide for an endoluminal prosthesis for placement in a body lumen having at least one segment of curvature wherein at least a portion of the body of endoluminal prosthesis is adapted to the size and shape of the body lumen. The endoluminal prosthesis further comprises features to better adapt to the body lumen, including, but not limited to apertures, tapering, beveling, non-circular cross-sections, flaring or branching of the body of the prosthesis.

Another object of the invention is to provide for a method of fabricating an endoluminal prosthesis having a body with at least one segment of curvature along a portion of the body.

A further object of the invention is to provide for a method of delivering and orienting an endoluminal prosthesis having a body with at least one segment of curvature along a portion of the body.

In a preferred embodiment, the present invention is an endoluminal stent having at least one segment of curvature along a portion of the body of the stent wherein the stent is sized and shaped to adapt to the anatomical features of the body lumen into which it is to be placed. The stent may further include such features as apertures, tapering, beveling, non-circular cross-sections, flaring or branching of the body of the prosthesis. The stent is fabricated using a shape-memory alloy wire or superelastic alloy wire. The anatomically correct stent is fabricated by wrapping wire in a helical manner around a curved, anatomically shaped mandrel, heat setting the wire while on the mandrel and removing the wire from the mandrel by unwrapping the wire such that upon removal from the mandrel, the wire reforms itself into the heat set shape. The stent may have markers to allow for imaging and orientation of the stent into the body lumen. The stent is delivered into the body lumen by a minimally invasive delivery system such as a catheter.

The present invention is not limited to the description provided herein. The description and drawings together will provide many of the preferred and possible embodiments, yet they are not meant to limit the scope of the invention.

BRIEF DESCRIPTION OF THE DRAWINGS

FIG. 1A illustrates the endoluminal prosthesis of the present invention wherein a portion of the body of the prosthesis is curved in one plane of curvature.

FIG. 1B illustrates a close-up view of the suture formed connection between the apices of the undulating wire utilized in the fabrication of the endoluminal prosthesis of the present invention.

FIG. 2 illustrates one embodiment of the wire used in the fabrication of the preferred embodiment of the present invention.

DESCRIPTION OF THE PREFERRED EMBODIMENTS

Figure 3A:
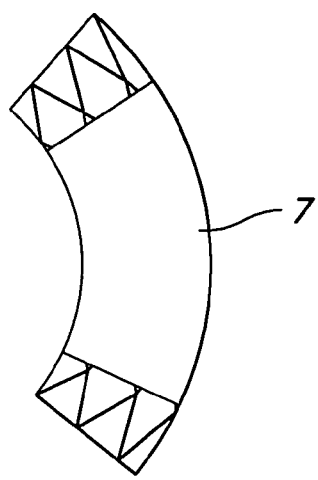
FIGS. 3A and 3B illustrate the endoluminal prosthesis of the present invention wherein at least a portion of the prosthesis is covered with a graft covering.

FIG. 1 shows a side view of a stent 1 in which the axis of the stent bends away from a straight line and is curved from the proximal end of the stent to the distal end. This curve is designed to match the natural anatomical geometry of the body lumen which is to be stented. The stent of the preferred embodiment is fabricated by twisting an undulating wire in a helical pattern around an anatomically correct mold or mandrel. The wire may be made of any biocompatible alloy including shape memory alloys and superelastic alloys. This stent has the apices 3 of each successive row connected to one another to form the tubular structure of the stent. These apices are connected by sutures 2 as highlighted in FIG. 1A, but they may be connected by any other manner as is known in the art such as welding. FIG. 2 shows the unrolled wire 5 with the V-shaped undulations 4 and apices 3. Wire 5 may also be provided straight, without undulations. The stent may also be manufactured by laser cutting a metal hypotube. The stent may be fabricated of nitinol, stainless steel, titanium, platinum, pyrolitic carbon or any other biocompatible metal or biocompatible ceramic as is known to the arts. The stent or wire may be made of polymers such as polyglycolic acid, expanded polytetrafluoroethylene or ePTFE, ployethylene terephalate, polylactic acid or any of the biocompatible polymers as are well known in the art. As well, the stent may be made of a biological material such as collagen, elastin, chitin or any of the biocompatible, biological materials as is known in the art. The stent may be made of any combination of these materials or of layers and varying constructs of these materials as is desired for performance of the stent. The stent may be a permanent or temporary implant. It may be fully dissolving, partially dissolving or non-dissolving. The stent may have a coating or multiple coatings. The stent may deliver pharmacological agents, genes, proteins, growth factors, hormones or any desired agent.

Figure 3B:
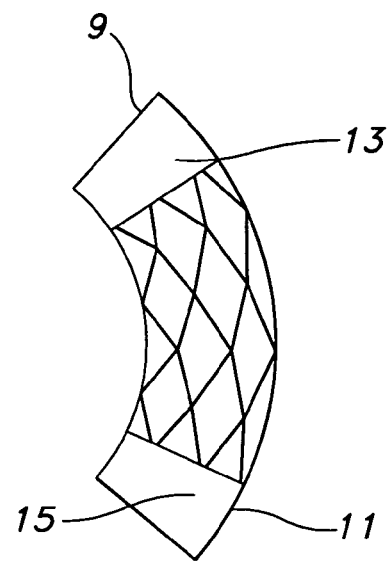

The stent may have a graft covering 7 as seen in FIG. 3A. The covering may cover a portion of the stent or may fully cover the stent. FIG. 3B shows a stent with only ends 9 and 11 covered by graft material 13 and 15. Typical graft materials include polyester, collagen and ePTFE. The covering may lie primarily on the outside of the stent, on the inside of the stent or both or between two coaxial stent scaffolds. The covering may be woven, braided, knitted, sutured or interwoven into the stent struts. The covering may be a solid tube slid over or into the stent or it may be a fabric that is wrapped around the stent and sealed. As well, the covering may be molded onto the stent, sprayed on or plasma deposited. The covering may be provided to the wire prior to forming the stent. The covering may be porous or non-porous. The covering may be bioabsorbable, partially bioabsorbable or non-bioabsorbable. The covering may contain pharmacologically active agents such as drugs or genes which are infused into, coated onto or temporarily placed onto it. The covering may have inherent pharmacologically advantageous properties or may have drugs, genes or other materials manufactured into the base material.

The stent may be constructed as per any of the methods that are practiced in the art. The stent may be formed by twisting, weaving, knitting or braiding materials or fibers. The stent may be a laser cut or electrically etched or mechanically cut tube. The stent may be formed by molding, dipping, or lost wax processes. It may be formed by lithography, sintering or vapor deposition of materials. The stent fabrication may include such manufacturing methods as welding, gluing, brazing, twisting, melting, mechanical locking, interference fitting or tying. Other stent fabrication processes may include cold-working, heat treating, chemical etching, dissolving, coating and processes necessary for preparing the stent for delivery such as freezing or crimping the stent.

Figure 4:
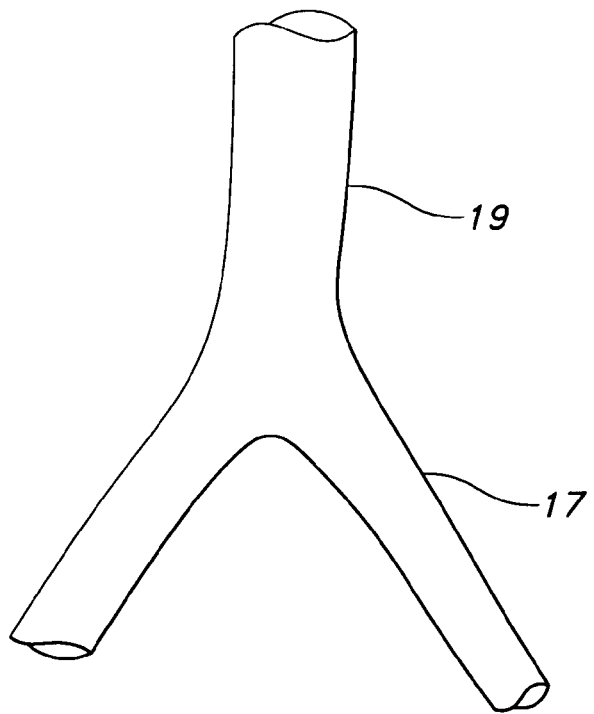
FIG. 4 illustrates the aorta and branchings of the iliac arteries in the human body.

A typical example of a body lumen that may have a natural bend in it is the iliac artery of the upper leg as shown in FIG. 4. The iliac artery 17 feeds off distally from the aorta 19. The iliac vessel is approximately 4 mm in diameter, with a range of 2 mm to 10 mm. The length of the vessel is approximately 150 mm. Over the total length, the vessel may bend up to 30 degrees from the original direction of the central axis and it will taper along its length, especially in the distal direction. Depending on the length of an implanted stent, the stent could impart an unnecessary straightening effect on the vessel. The straightening forces could result in any number of short or long term complications as were described above. A typical length of the stent in this location would be from 50 mm to 130 mm.

Figure 5:
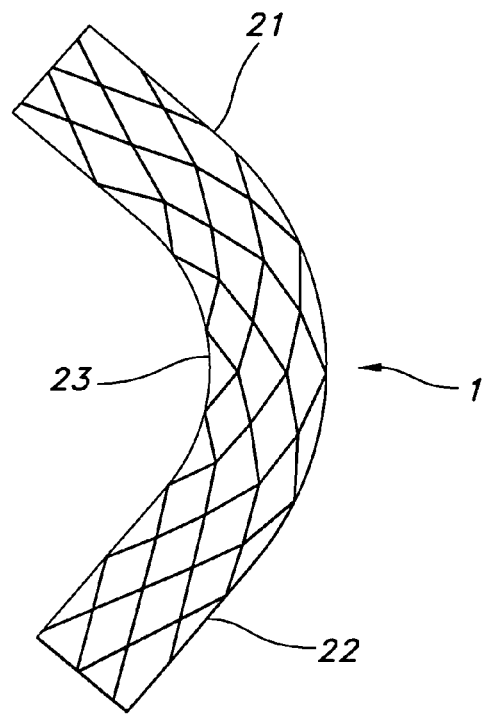
FIG. 5 illustrates a typical endoluminal prosthesis of the present invention having a curved portion in the middle segment of the body and straight portions at each end of the body.

FIG. 5 shows stent 1 of FIG. 1 as manufactured for placement in an iliac vessel, such as iliac artery 17. The manufactured shape of the stent may not be sized to the exact anatomical shape of the vessel in which it is to be applied. The most feasible approach to the development and marketing of a curved stent is to create a series of stent sizes with preformed curves that approximate a general range of anatomical geometries. Straight stents are generally catalogued with respect to length and diameter. Typical cataloged stent sizes for a straight iliac stent are 6, 8 and 12 mm in diameter and 60, 80 and 100 mm in length. A curved stent product in a catalogue would further refer to the curvature or shape of the stent in a general sense.

Figure 6A:
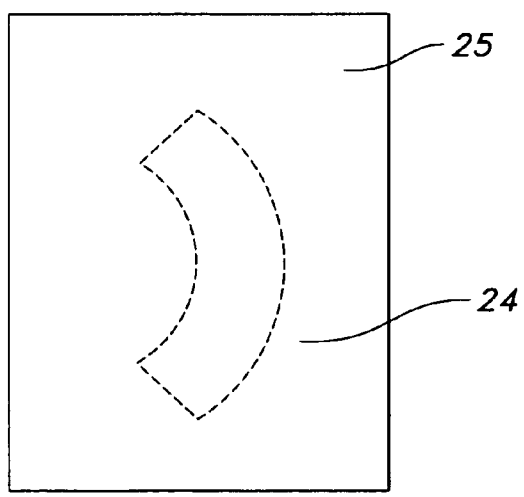
FIGS. 6A and 6B illustrate image projections of the endoluminal prosthesis of FIG. 5. in imaging planes that are perpendicular to the plane of curvature and parallel to the plane of curvature.
Figure 6B:
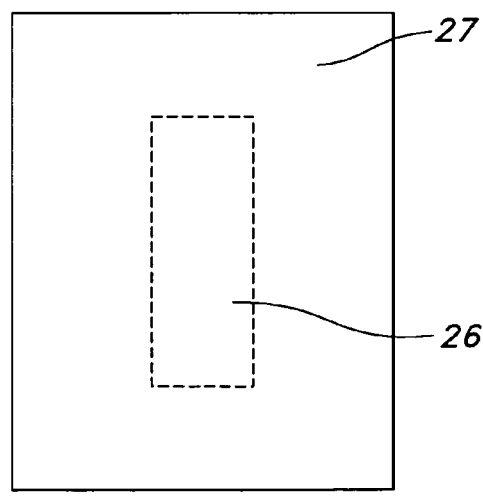
Figure 7A:
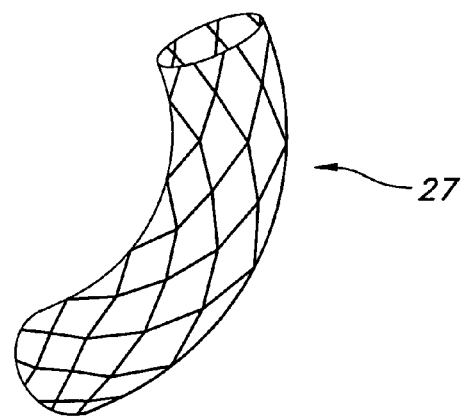
FIG. 7A illustrates an axiometric view of a three dimensionally curved endoluminal prosthesis curved in two planes of curvature.
Figure 7B:
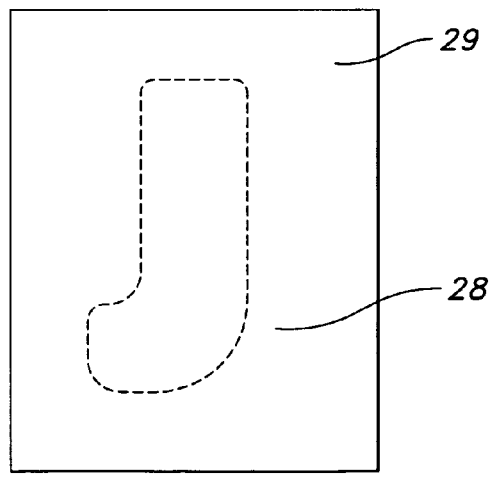
FIGS. 7B and 7C illustrate imaging projections 90 degrees apart from one another around the axis of the three dimensionally curved endoluminal prosthesis of FIG. 7A.
Figure 7C:
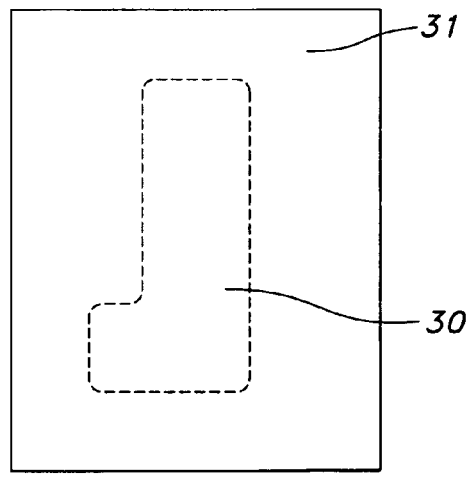

The stent 1 in FIG. 5 includes a straight segment 21 followed by a curved segment 23 and finally a straight segment 22. Curved segment 23 is curved in only one plane. A stent of the nature of that shown in FIG. 5 would be identified by the diameter and overall length of the stent and then the details as to the length of each straight and curved segment, the location of the beginning and end of the curve and the radius of curvature of that curve. Curved stents may be visually identified or catalogued by offering a projection of the stent in the plane of curvature as seen in FIGS. 6A and 6B. A curved stent 1 that is curved in one plane would present the curve in a projection 24 that is perpendicular 25 to the curve, but would present a straight projection 26 in a plane that is parallel 27 to the curve. A curved stent 32 that is curved in two planes, as is illustrated in FIGS. 7A, 7B and 7C, would present the curvature in both planes, perpendicular 29 to the curve and parallel 31 to the curve shown as projections 28 and 30, respectively.

Figure 8A:
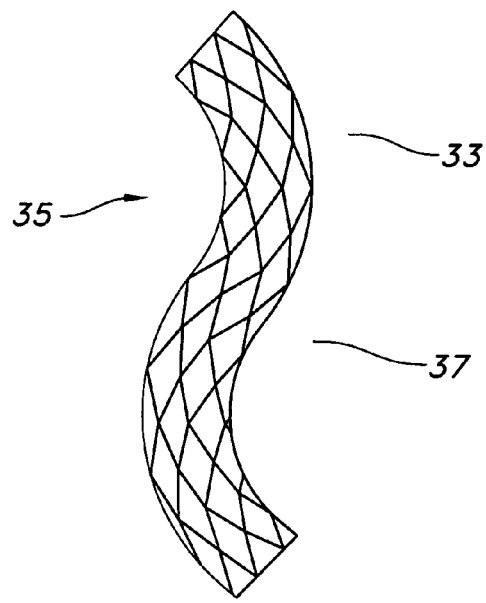
FIG. 8A illustrates an endoluminal prosthesis having two curves placed successively along the body of the prosthesis and lying in the same plane of curvature.
Figure 8B:
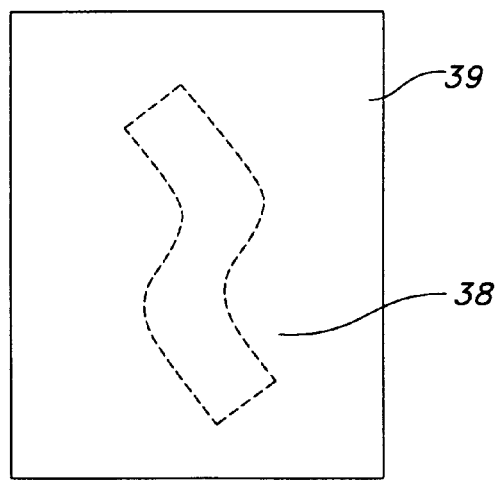
FIGS. 8B and 8C illustrate imaging projections 90 degrees apart from one another around the axis of the three dimensionally curved endoluminal prosthesis of FIG. 8A.
Figure 8C:
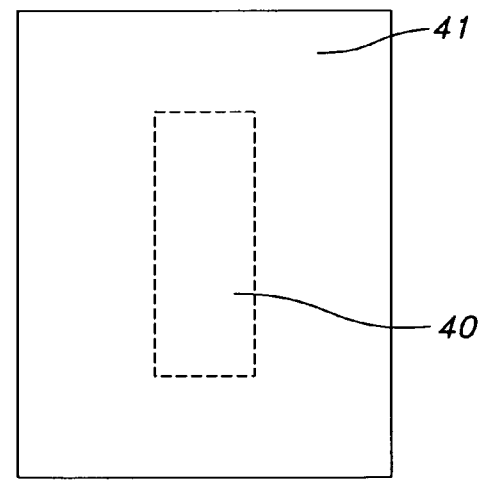

FIG. 8A illustrates stent 33, having more than one curve in succession, curves 35 and 37, yet both curves fall in the same plane 39. Curves 35 and 37 are located in progressive succession along the body of stent 33. The image projection 38 of stent 33 in perpendicular plane 39 is illustrated in FIG. 8B and the projection 40 in the parallel plane 41 is illustrated in FIG. 8C. Once again the identification of this stent would include the stent diameter and overall length as well as the individual lengths of each straight segment and curve, the beginnings and ends of each curve and the radius of curvature of each curve.

Figure 9A:
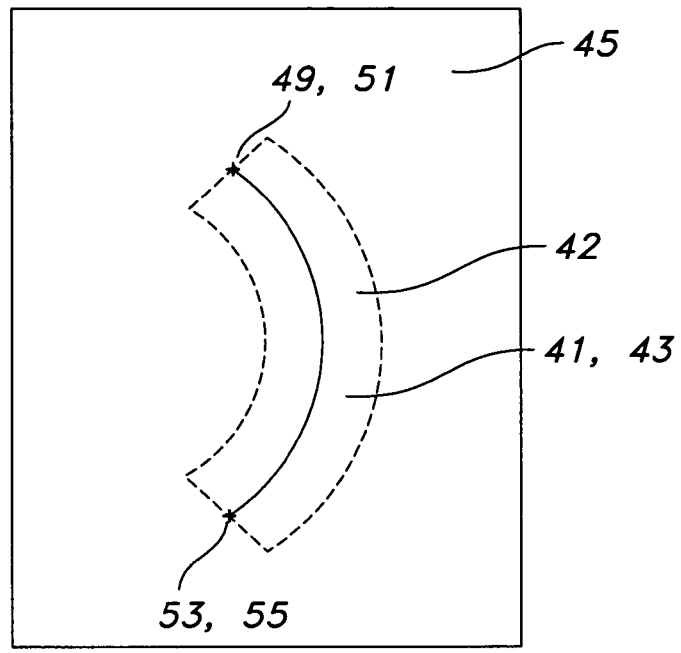
FIGS. 9A and 9B illustrate imaging projections 90 degrees apart from one another around the axis of the of the stent of FIG. 5 and feature imaging markers and lines to allowing identification and orientation of the curved endoluminal prosthesis in vivo.
Figure 9B:
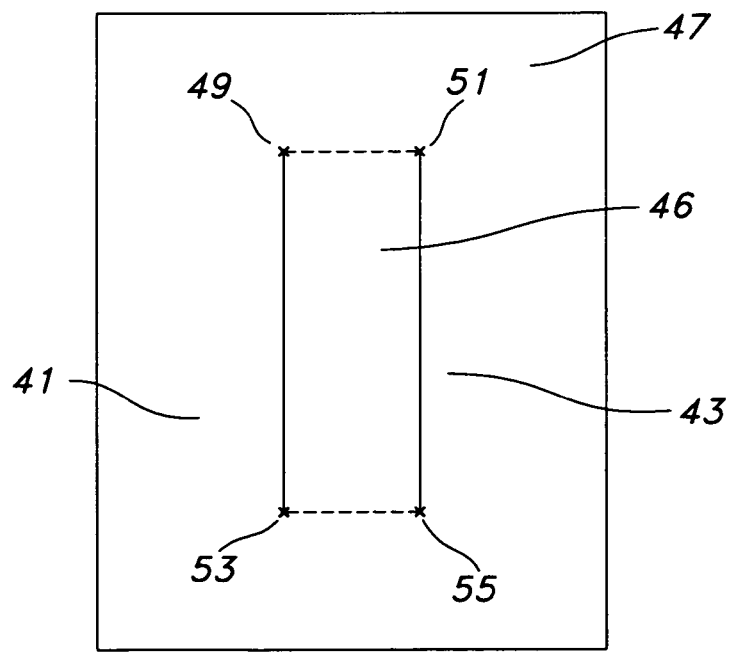

The stents and their curves as shown in FIGS. 5, 6, 7, and 8 would be best identified in situ on imaging systems by use of visible markers. A stent orientation marking scheme is important for the correct positioning of this anatomically correct stent in the vessel. Commonly used imaging systems include fluoroscopy and MRI. The best method of marking the curved stent would be to identify the curve of the stent, as is illustrated in FIG. 9A, by two marking lines 41 and 43 that are visible by imaging running parallel to the curve of the stent. FIGS. 9A and 9B show two perspectives of the stent with the marking lines 41 and 43 in this orientation with respect to perpendicular plane 45 and parallel plane 47. Perpendicular projection 42 illustrates marking lines 41 and 43 as overlapping whereas parallel projection 46 illustrates marking lines 41 and 43 at opposite ends of the curved stent. For purposes of the most common medical implant marking system, these markers would preferably be radiopaque, RO, markers. The lines can be formed of RO filaments interwoven into the stent body, with RO paint along the body of the stent, with successive RO markers or with any method as is commonly practiced. At each end of the two RO lines, an RO marker would be placed to identify the beginning and end of the marking lines. These RO markers are typically small pieces of radiopaque material such as platinum that are crimped to the structure of the stent, but may be any type of marking as is commonly known in the art. Markers 49, 51, 53 and 55 are shown in FIGS. 9A and 9B as identifying the ends of RO lines. This arrangement of RO markers and lines as shown in FIGS. 9A and 9B allow the physician to identify the exact orientation of the stent curve by taking an image in one plane, such as plane 45, and identifying the true curve as the imaging angle in which the two lines overlap exactly, as is seen in FIG. 9A. At this point, the imaging system is known to be exactly perpendicular to the plane of curvature. FIG. 9B illustrates how the stent orientation may be further characterized by imaging its position at 90 degrees about its axis from the perpendicular projection of FIG. 9A.

Figure 10A:
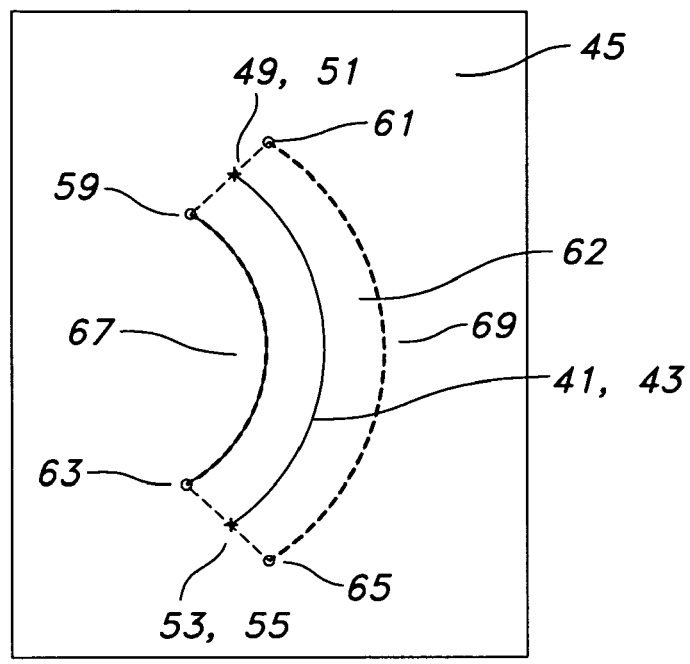
FIGS. 10A and 10B illustrate imaging projections 90 degrees apart from one another around the axis of the of the stent of FIG. 5 and feature imaging markers and lines to allowing identification and orientation of the curved endoluminal prosthesis in vivo. These drawings illustrate additional imaging lines to further assist the orientation process.
Figure 10B:
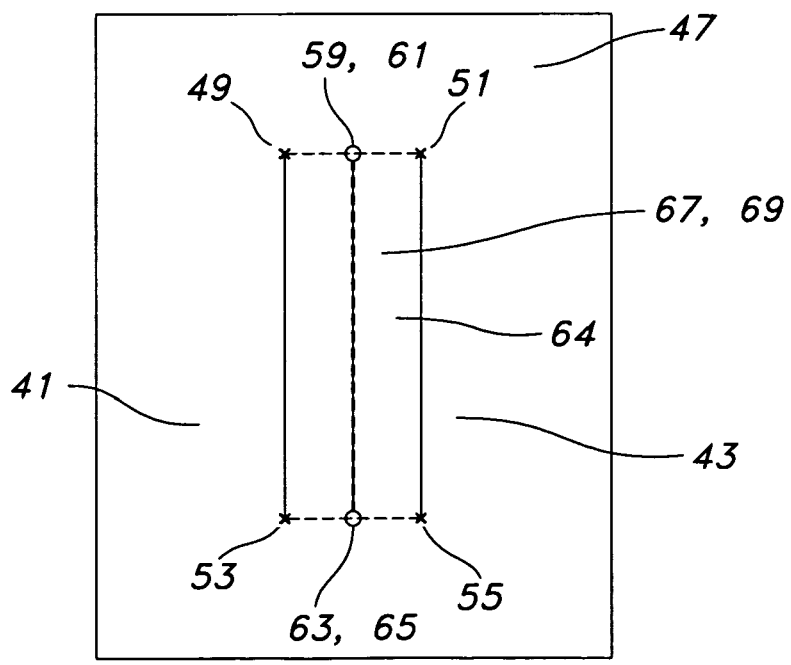

The marking system may further include marking lines and markers running exactly along the plane of curvature, 90 degrees in axial rotation on the stent body from the curve positioning markers 49 and 51 as is illustrated in FIG. 10A which is an image plane 45 aligned perpendicular to the original axis of the stent having stent image 62. Markers 59 and 61 indicate the origin of RO marking lines 67 and 69. FIG. 10B illustrates the parallel plane 47 and image projection 64 with the two RO marking lines 67 and 69. The ends of RO marking lines 67 and 69 are marked at the proximal end, or origin, of the curved stent by markers 59 and 61 and at the distal end by markers 63 and 65. In FIG. 10B, the two proximal markers 59 and 61 overlap and the two distal markers 63 and 65 may overlap, indicating the direct alignment of the imaging system in the parallel plane, along the inside and outside spines of the curve.

Figure 11:
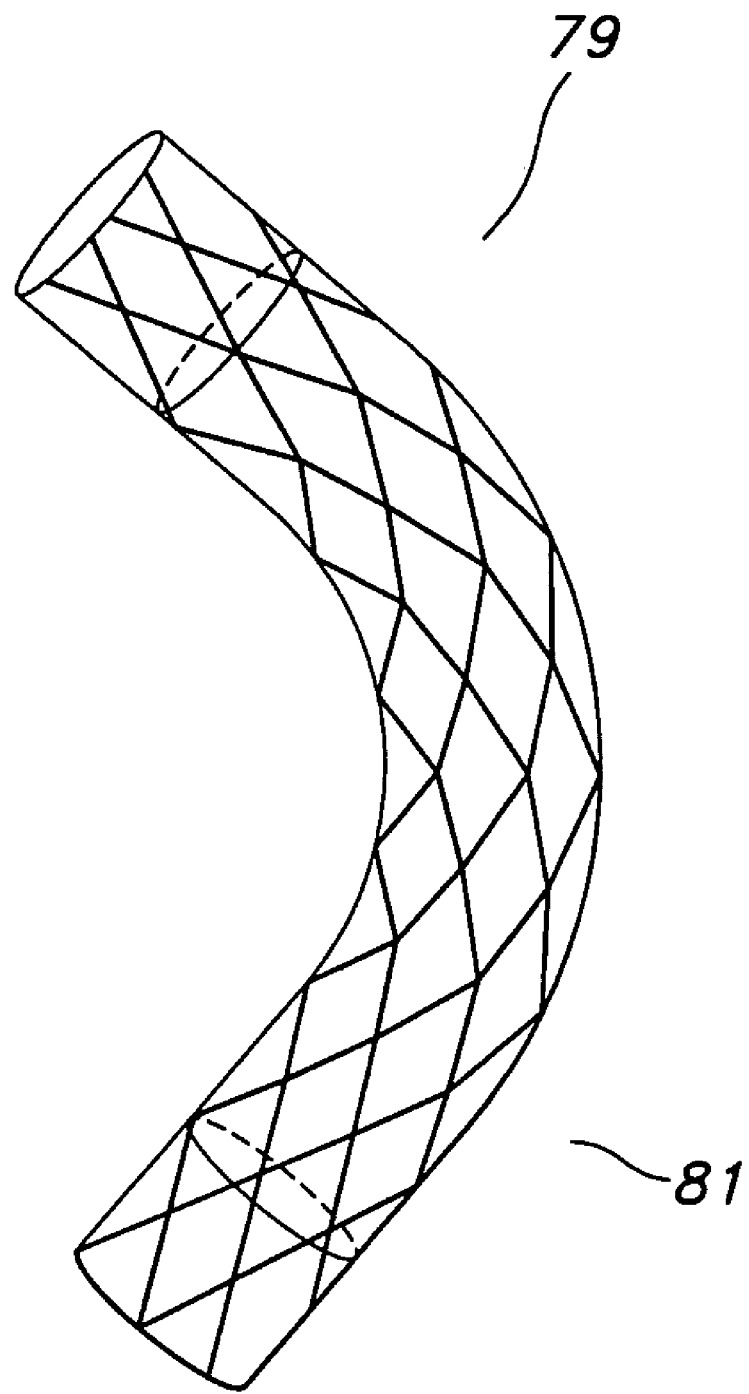
FIG. 11 illustrates the use of circumferential imaging markers on a curved endoluminal prosthesis of the present invention.

FIG. 10A portrays the perpendicular plane 45 and perpendicular image projection 62 of the curvature of the stent. RO marking lines 41 and 43 are in perfect alignment here indicating a true image of the curve. Lines 41 and 43 have proximal markers 49 and 51 respectively at their origin and distal markers 53 and 55 respectively at their ends. This secondary marking system allows the physician to see the actual expansion size of the deployed curved stent. The RO markers 59, 61, 63 and 65 are best designed as having a different shape than the RO markers 49, 51, 53 and 55 so as to allow the physician the ability to understand the three dimensional positioning of the curved stent in two dimensional space. As well, marking lines 67 and 69 would be best designed with a slightly different geometry than marking lines 41 and 43. An example would be fat lines and dotted lines to distinguish one from another. It is possible as well to indicate the dilated position of the stent using markers running the circumference of the stent 79 and 81 rather than or in addition to RO lines 41 and 43. Circumferential markers 79 and 81 are illustrated in FIG. 11 as placed on curved stent 1.

Figure 12A:
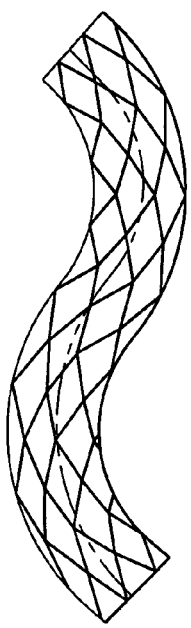
FIG. 12A illustrates an endoluminal prosthesis having two curves placed successively along the body of the prosthesis and lying in the same plane of curvature including image markers and lines to assist in identification and orientation of the prosthesis.
Figure 12B:
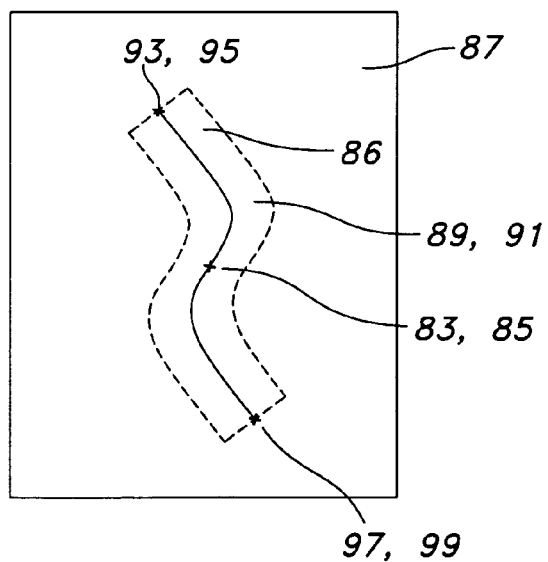
FIGS. 12B-12E illustrate image projections of the endoluminal prosthesis of FIG. 12A including various marking schemes to assist in identification and orientation of the prosthesis.
Figure 12C:
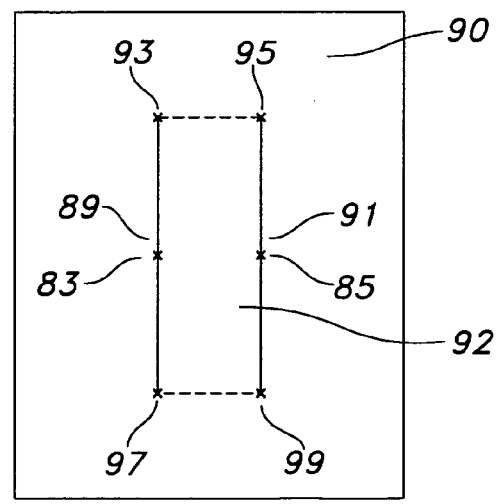
Figure 12D:
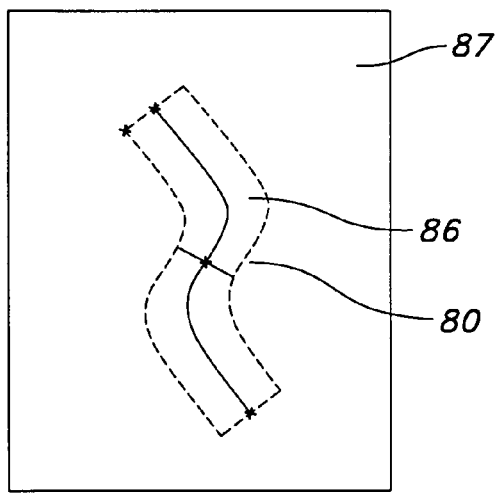
Figure 12E:
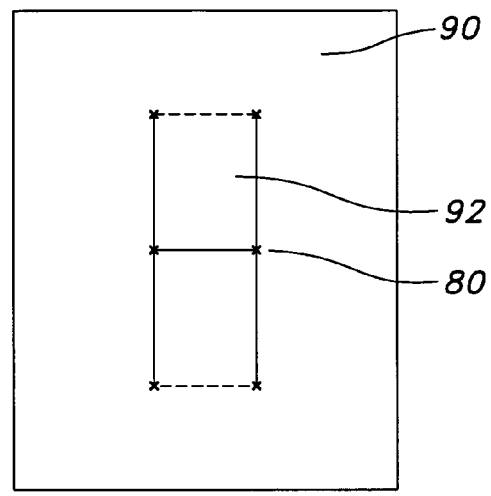

When more than one curve is present in the same plane and in series with at least one other curve in that plane, the successive curvatures may be identified using one common set of RO lines, one common set of end markers and a new set of intermediate markers 83 and 85 identifying the change in curvature. FIGS. 12A, 12B and 12C illustrate a curved stent having more than one curve in the same plane along the length of the stent body in the isometric, perpendicular and parallel views respectively. Once again, the perpendicular plane of projection 87 and image projection 86 as illustrated in FIG. 12B shows curve marking lines 89 and 91 as overlapping when their projection is true, identifying the curvature of the stent. FIG. 12C provides a parallel projection 90 and imaging projection 92 of the stent. In the parallel projection, it is possible to clearly identify the proximal markers, 93 and 95, the distal markers 97 and 99, the intermediate markers 83 and 85 and the two RO marking lines 101 and 103. The beginning of the second curve may also be indicated by use of a circular marking 80 as illustrated in the projections 86 and 92 shown in FIGS. 12D and 12E.

Figure 13A:
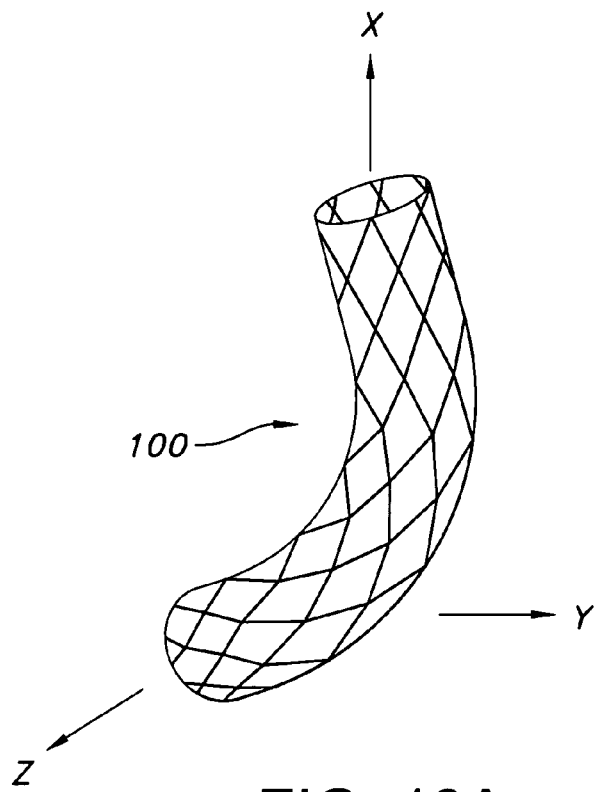
FIGS. 13A and 13B illustrate two axiomatric views of an endoluminal prosthesis having two segments of curvature wherein each segment lies in a different plane of curvature and the two segments overlap.
Figure 13B:
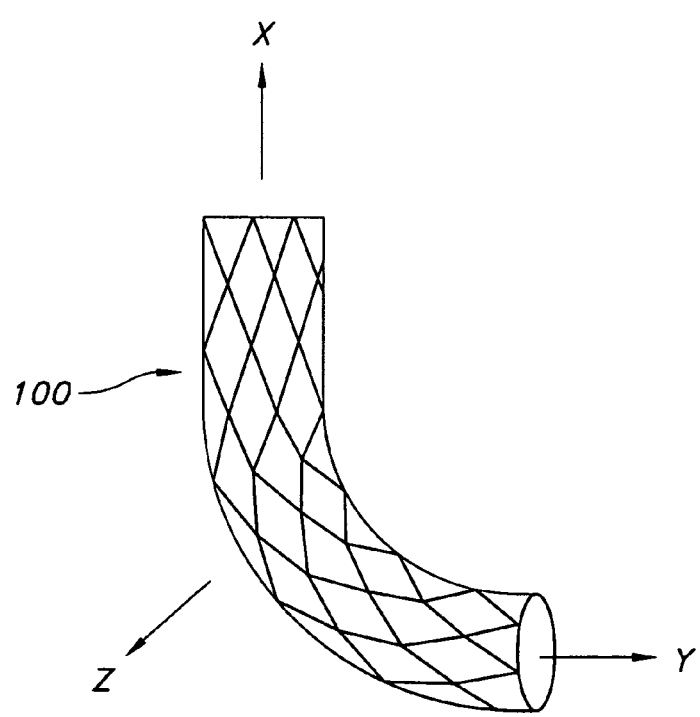

The most accurately shaped anatomically correct stents will have a three dimensional curvature. FIGS. 13A and 13B illustrate an isometric view of a three dimensionally curved stent 100. Identifying the multi-dimensional stent position in vivo is more difficult than with a stent curved in one plane. The segments of curvature along the body of a three dimensionally curved stent may overlap in total or for only a portion of each curve within each plane of curvature. As mentioned above, it is possible to define the three dimensional curve using superposition of two different curves aligned in the perpendicular plane and parallel plane. The orientation of the anatomically correct stent curved in a single plane is readily identifiable by use of marking lines. The same concept applies to a stent curved in two planes, however, the marking lines along each plane of curvature will not be aligned when the curve is projected as they had in single plane curvature. As well, the trace of the curve as was possible in a single plane curve as illustrated in FIG. 10A is no longer feasible. The marking lines will now include the curvature of the stent in the second plane.

Figure 13C:
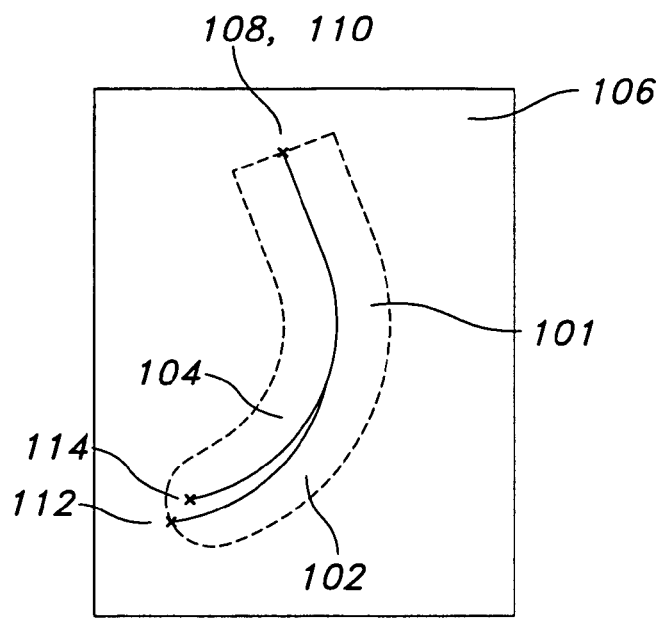
FIGS. 13C and 13D illustrate two image projections of the endoluminal prosthesis of FIGS. 13A and 13B. The two projections are 90 degrees relative to one another.
Figure 13D:
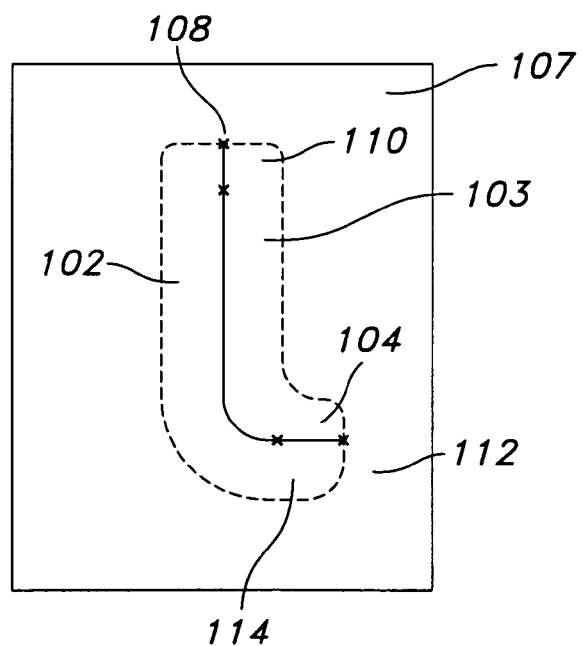

To avoid confusion between perpendicular plane and parallel plane marking lines, different shape markers at the ends of the lines may be used, as well as any marking system known in the art. FIG. 13C illustrates imaging projection 101 and the alignment of two marking lines 102 and 104 in one plane of curvature 106. These two lines will overlap until the second curve begins. The second curve misaligns the marking lines on the projection. The initial image can be found either by an indicator on the delivery system to aid in orientation and imaging or by trial and error. If by trial and error, the correct imaging plane will be evident when an initial portion of the two marking lines overlaps. The second projection of curvature is found by rotating the imaging system 90 degrees. The orientation of the three dimensionally curved stent is confirmed by the marking lines and by providing the physician with a diagram of the marking lines in the initial projection and at 90 degrees to the initial projection. FIGS. 13C and 13D illustrate image projections 101 and 103 of stent in plane 106 and 107 aligned 90 degrees relative to one another. There is no real distinction as to parallel to a curve or perpendicular to a curve when curves in more than one plane intersect in three dimensional imaging. Marking lines 102 and 104 will only partially overlap depending on the imaging angle. Markers 108, 110, 112 and 114 will not consistently overlap as was portrayed with respect to two dimensional curves, that is to say, curves in the same plane of reference.

In all cases of curvature alignment the final image will have some error associated with the inexact fit of the anatomically curved stent into the curved vessel. This will be especially true in the case of preformed curves and size ranges. The level of misalignment will be indicated either by the projections found with respect to the projections expected.

In any event, armed with the orientation information, the physician may chose to remove the anatomically correct stent and re-deploy another stent. The stent may be designed to allow removal or repositioning using any of the methods as commonly known in the art. One such method is by a use of the sheath on the delivery system for deployment of the stent. If a portion of the stent is inside the sheath of the stent delivery system when the stent is under deployment, the physician will have the option to rotate the deployed portion of the stent by torquing the stent delivery system from the handle ex-vivo. Preferably the physician would deploy a portion of the stent, image the relative orientation by use of the marking lines and re-cover the stent with the sheath if a new position is necessary. The sheath itself may have RO markers and marking lines to establish the initial positioning of the un-deployed anatomically correct stent. An additional embodiment to allow recapturing a portion of the stent is to have the stent only partially expand, such that twisting the stent does not allow for too much contact of the stent against the vessel wall. In the case of a partially expanded anatomically correct stent, the markers will have to be defined such that they can indicate the correct position even in the incompletely deployed stent. Partial expansion may be controlled in different manners as is known in the art. Embodiments include the use of balloon expandable or plastically deformable stent materials in conjunction with self-expanding or elastic stent materials to allow the stent to only partially deploy upon initial position and sheath withdrawal. An alternative partial expansion embodiment is to provide restriction bands along the length of the stent that do not allow full expansion of the stent until positioning is finalized. At this point, the bands would be broken by balloon dilation or the like. The methods of stent deployment and partial expansion mode presented herein serve only as examples and are not meant to restrict the possible stent deployment techniques available for the anatomically correct stents.

Figure 14A:
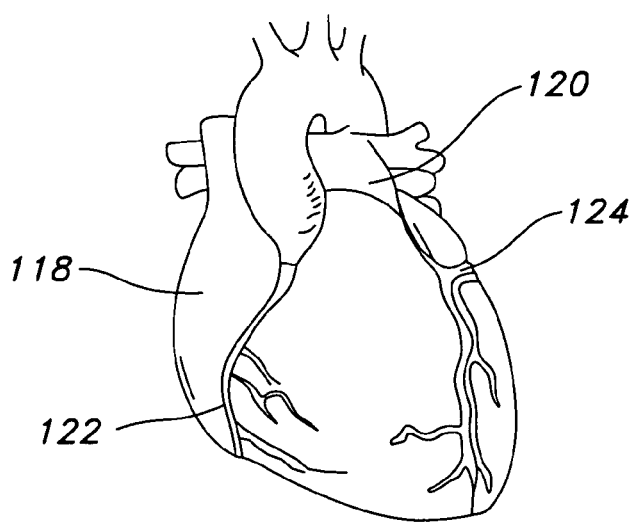
FIGS. 14A and 14B illustrate two views of a human heart, the coronary vessels located on the external surface of the heart and the curves and branchings of these vessels.
Figure 14B:
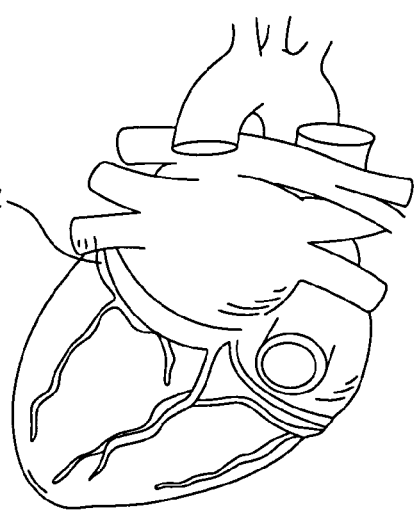

Other vessels having a high rate of curvature include coronary arteries. These vessels wrap around the outside of the heart. FIGS. 14A and 14B in an anterior view and a posterior view of the heart 118 respectively. The larger coronaries include left coronary 120, right coronary 122 and the left circumflex 124. These vessels have a high degree of curvature, both to maintain a wide delivery area of blood flow to cardiac tissue and as well because of the natural curvature of the heart. Coronary arteries may follow a path up to 90 degrees from the initial direction as they progress. As well, the perimeter of the heart may add a second curvature, which would be less than 45 degrees due to typical stent lengths of 10 mm. Coronary artery diameters range from 1 mm to 5 mm with a typical size of 3 mm. These arteries all have associated main branches. Coronary vessels often suffer from arteriosclerotic lesions which are frequently treated by stent placement within the vessels. Coronary arteries naturally open and close during the cardiac cycle due to the intermittent compression of the cardiac tissue on the vessel. These vessels are very small in diameter and very sensitive to thrombosis or injury. The ramifications of an occluded coronary artery include reduced blood flow to cardiac tissue which may lead to a coronary infarction and possibly ischemia. As these vessel are quite small and prone to intravascular injury during interventions as well as restenosis following intervention, the application of an anatomically correct stent will improve the treatment success by reducing the factors that may encourage restenosis and thrombosis.

Figure 15:
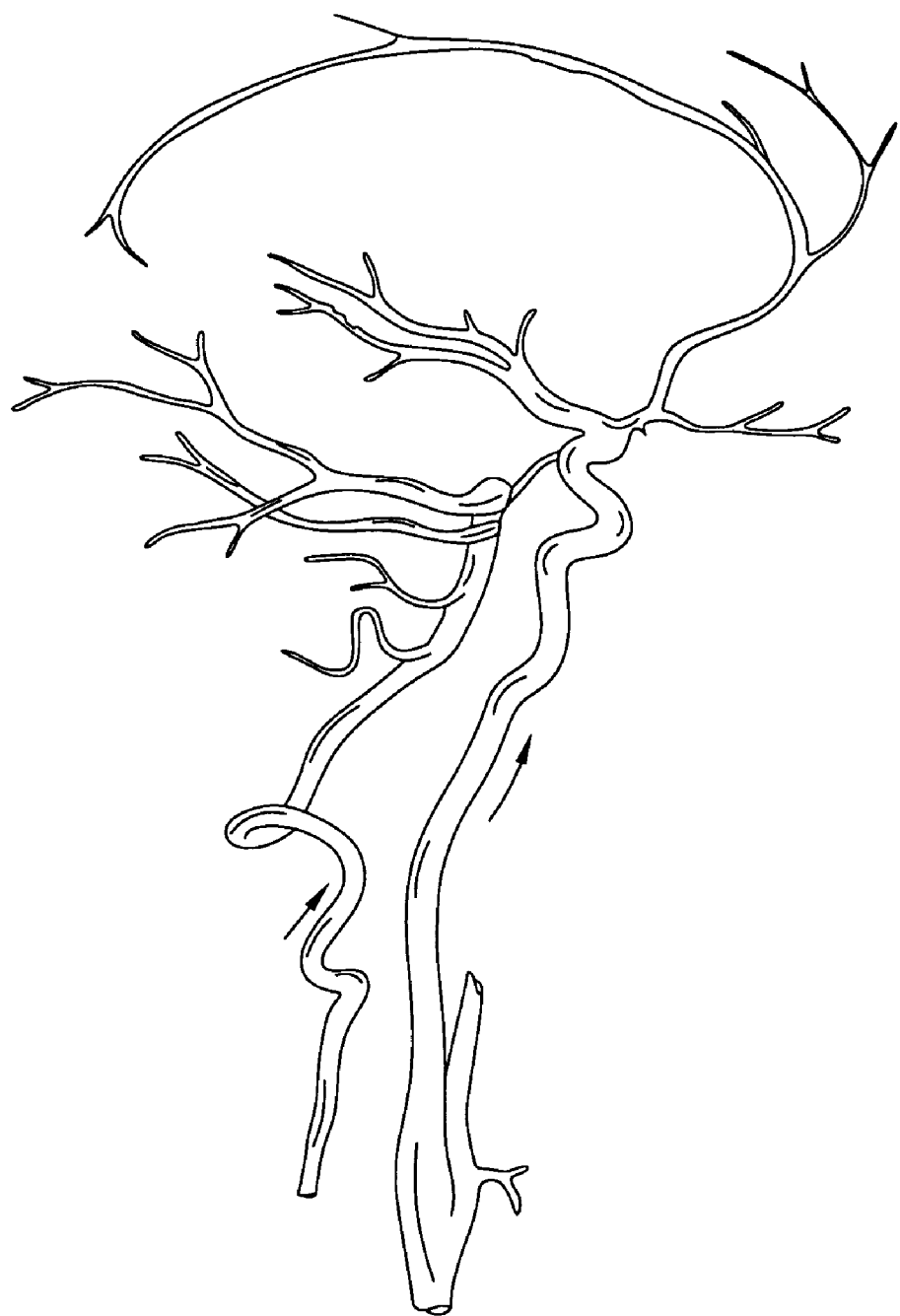
FIG. 15 illustrates the anatomy of an area of the cerebral vessels as well as the curves and branchings in those vessels.

Another set of highly curved vessels are the cerebral or brain vessels, a view of which is shown in FIG. 15. The cerebral vessels are branches of the left and right carotid arteries extending from the aorta and into the head. These blood vessels are some of the smallest in the body and their patency is crucial to the functioning of the brain. Typical vessel sizes in the brain are 1-3 mm. The curvature here is very high; the vessels may actually twist and turn more than 360 degrees as they progress. Unlike in the heart, these vessels are not subjected to surrounding contractile tissue. The vessels, however, are subjected to normal arterial pressures. Due to the sensitive nature of these vessels, any attempt to alleviate unnecessary stress inside the vessel lumen is prudent when utilizing an implant. A small emboli in this anatomy could lead to a devastating health problem.

Figure 16:
FIG. 16 illustrates the human intestines and portrays the length and multiple curves of the intestine.

The intestines represent a lumen in the body which has a high level of curvature as seen in FIG. 16 and for which stent placement may be the correct treatment for a specific disease. In the intestines, diseases that may require stenting include tumors, anastomoses, ulcerations and restrictions causes by surrounding organs, injury or post surgery. Furthermore, stents may be used to administer a treatment agent to the intestinal lining by having the agent incorporated into the stent in any of the manners described above. When intestinal tissue is injured, scarred or diseased, the tissue is especially friable. This state renders the tissue more sensitive to forces applied upon it resulting in the possibilities of tearing, dissection of layers, irritation, inflammation, dysplasia or hyperplasia, as could occur with the application of a stent within the intestine. Typical intestinal sizes are dependent upon the anatomical site. The small intestine may range from 15 mm to 20 mm in diameter whereas the large intestine ranges from 20 mm to 40 mm in diameter. Intestines tend to fold back on themselves in a serpentine manner allowing for curves of up to approximately 180 degrees.

Yet another need for a curved stent is found at vessel branching or junctures. Most arteries both taper down in diameter and branch out into tissues as they progress. These branches may either be an offshoot of the artery or a division of the artery into two or more separate directions. In any event, branching often leads to a curve in the path of the vessel. Branching of vessels can be seen well in FIGS. 14 and 15, as is exemplified by the branching of the coronary arteries.

Figure 17A:
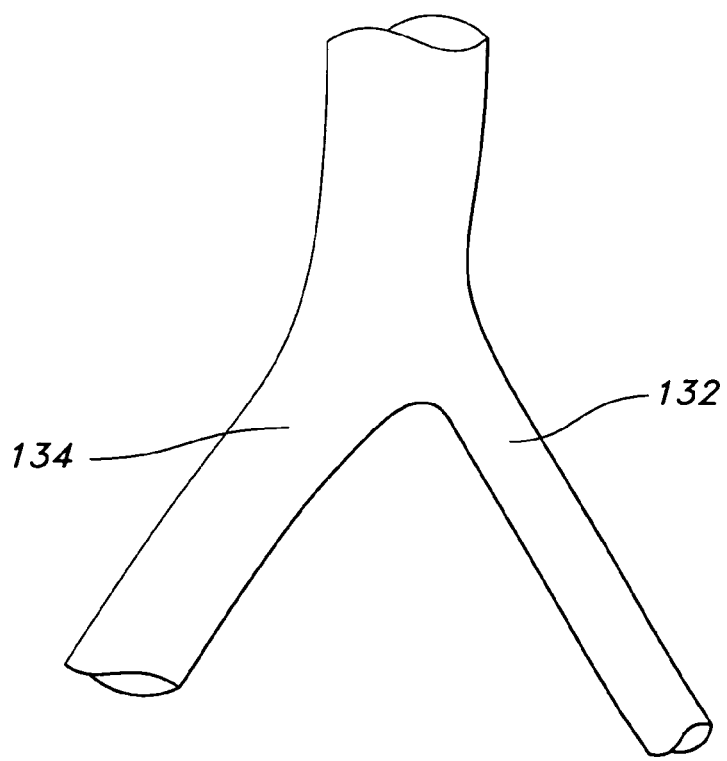
FIGS. 17A and 17B illustrate a branching vessel and the resulting vessel restriction resulting from placing a straight stent across the juncture of the two vessels.
Figure 17B:
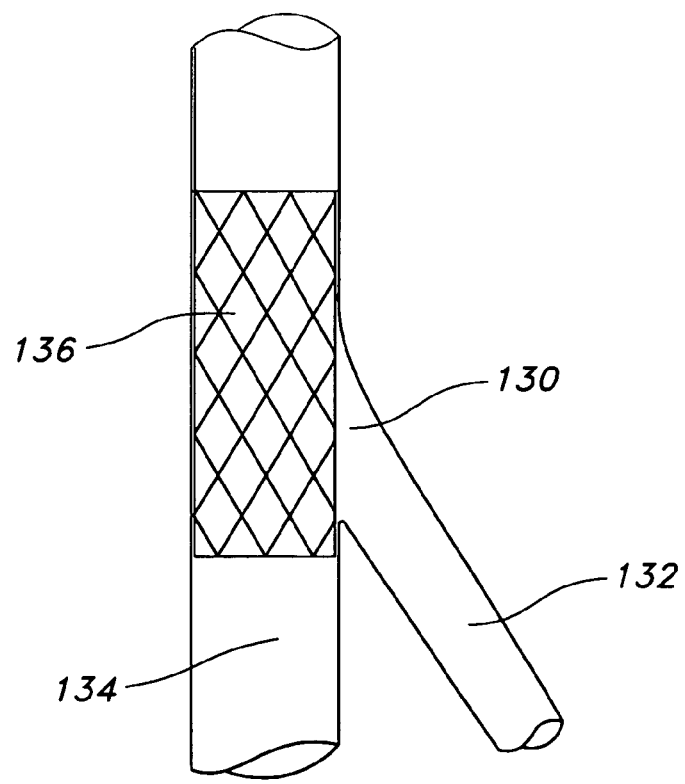
Figure 18A:
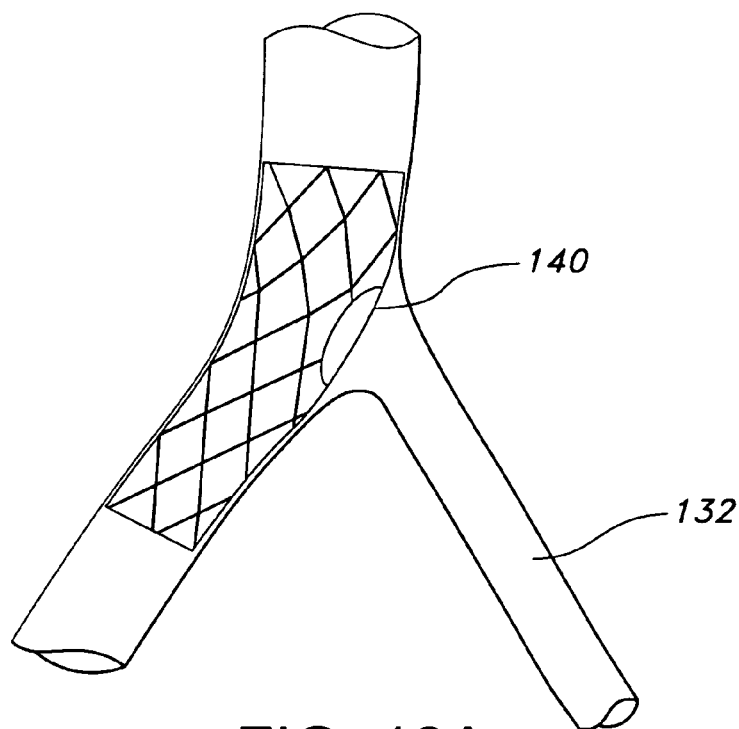
FIGS. 18A and 18B illustrate the placement of two anatomically correct endoluminal prostheses at a point of vessel juncture.
Figure 18B:
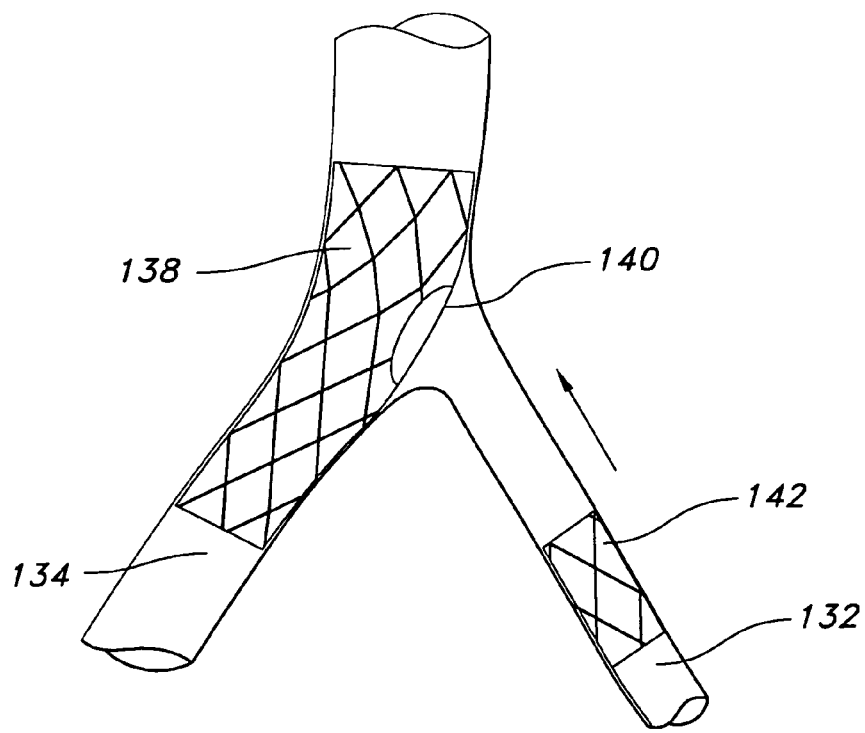

Vessel branching adds a further complication to the placement of straight stents. If a straight stent is placed along the vessel and across the point of juncture, it may straighten one branch of the vessel in such a way as to impinge upon the opening of the other branch of the vessel as is shown in FIGS. 17A and 17B. Constriction site 130 on vessel 132 would rise as a result of straight stent 136 influencing vessel 134 to push against vessel 132. A curved stent positioned into the vessel would accommodate the natural division of the vessel without affecting another leg. In a situation requiring a stent across a vessel division, the stent would have an aperture facing the direction of the non-stented branch. More than one anatomically correct stent may be used in a series, such as in vessels having frequent changes in curvature or in cases of vessel branching. With respect to vessel branching, a stent 138 having an aperture 140 located on the stent body may be placed with the aperture directed towards the branch juncture. The placement of the aperture may be accomplished by both imaging techniques and aperture markers as well as by indicators on the stent delivery system handle to direct the orientation of the aperture. A second anatomically correct stent 142 would then be placed with the origin of the stent aligned adjacent to or in connection with the first stent. FIGS. 18A and 18B illustrate the placement of two anatomically correct stents, 138 and 142 in an area of vessel branching.

Figure 19:
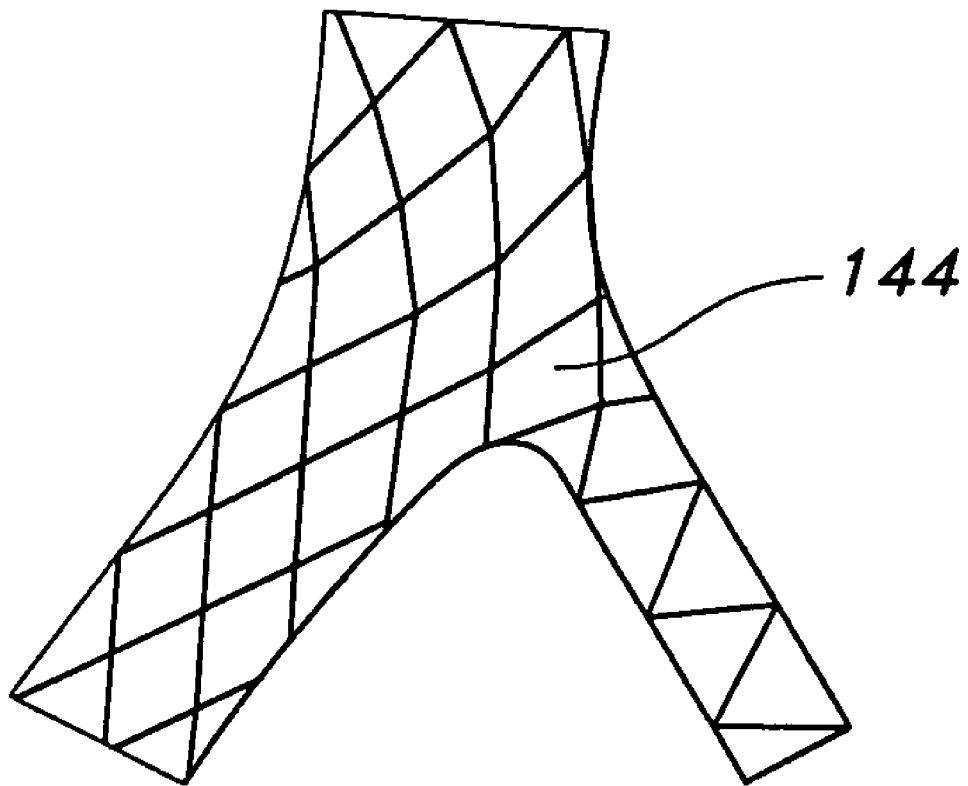
FIG. 19 illustrates an anatomically correct endoluminal prosthesis having areas of curvature and branching.

The opportunity exists as well to provide for a stent with a body portion that divides into 2 or more legs. The legs of this branching stent would be designed to align with the natural curvature of the root vessel and its divisions. In this manner, none of the branches from the root vessel would be affected by stent placement within another branch. FIG. 19 illustrates an anatomically correct stent 144 having more than one leg.

Figure 20:
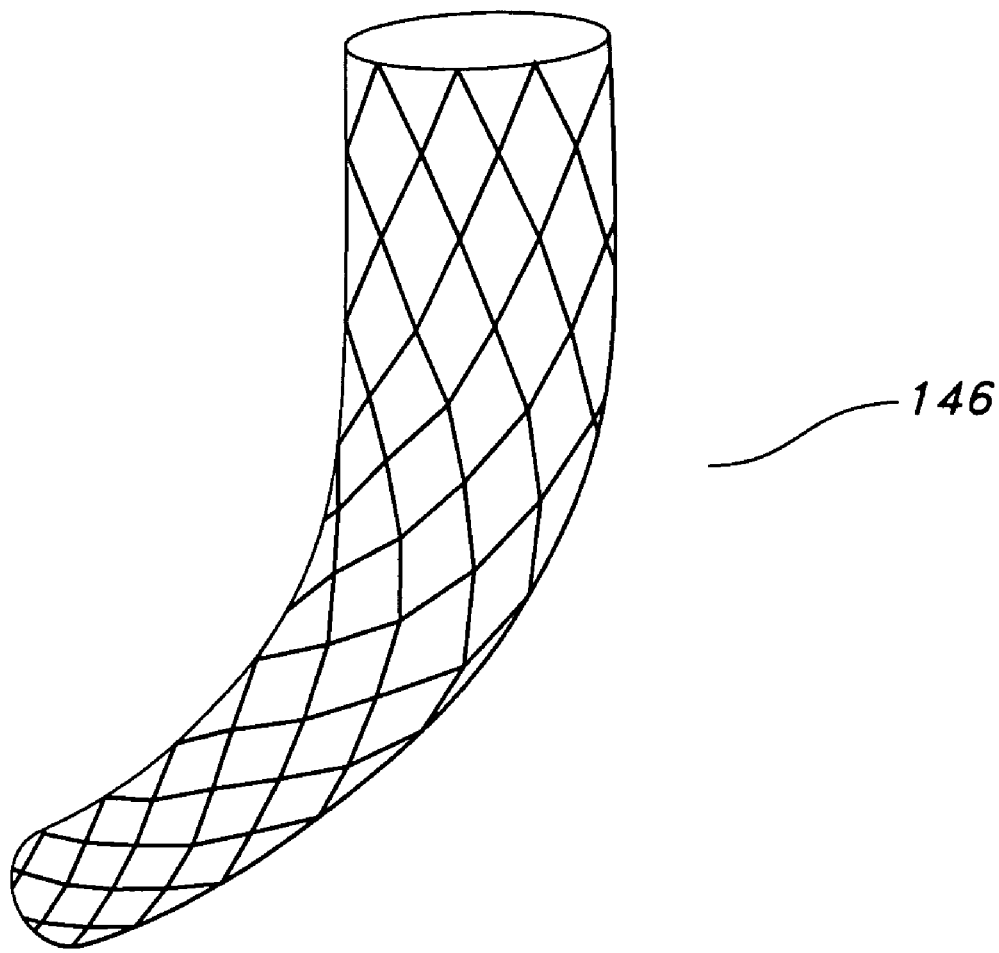
FIG. 20 illustrates an anatomically correct endoluminal prosthesis having areas of curvature and tapering.

It may be advantageous to create the anatomically correct stents with tapering of the diameter of the stent 146 along its length as seen in FIG. 20. Body vessels are known to naturally taper in the direction of blood flow, as they deliver blood to more remote sites in the body. Most commercially available stents are manufactured with a constant diameter across their length. This constant diameter will cause the stent to exert a higher force on the vessel in the area of a constriction in the vessel as may occur at a lesion, a natural tapering or a tortuosity. Obviously, it is desired to apply a sufficient amount of force on a lesion to restore a vessel to its natural diameter. Yet, in the case of the tortuosity or taper, this higher application of force may result in any of the complications mentioned above. To avoid unnecessary non-uniform distribution of the dilation forces along the length of the stent at sites of natural tapering or tortuosity, it is advantageous to make a stent that is smaller in diameter with respect to the tapered or tortuous area in the vessel to which it is to be applied.

Curved stent characterization would be identified by the straight distance from the proximal end of the stent to the curve origin on the stent body followed by the curve length and a radius of curvature. Curved stents may have straight sections at any point before or after areas of curvature. An example of a typical anatomically correct stent would include a length of 30 mm from curve end to end, with a radius of curvature, such as 25 mm, measured from the stent center axis and located midway along the curve stent. There may be a straight section leading into the curve and a straight section leading out of the curve. Stent size and shape data would then be transposed into a coded part or catalog number.

Along with dimensional characterization of an anatomically correct stent, the physician would be provided with a diagram indicating the orientation of the deployed stent in reference to the RO markers and lines as described above. FIGS. 9, 10, 12 and 13 illustrate some planar views of imaging projections of anatomically correct stents that could be provided to the physician.

Figure 21:
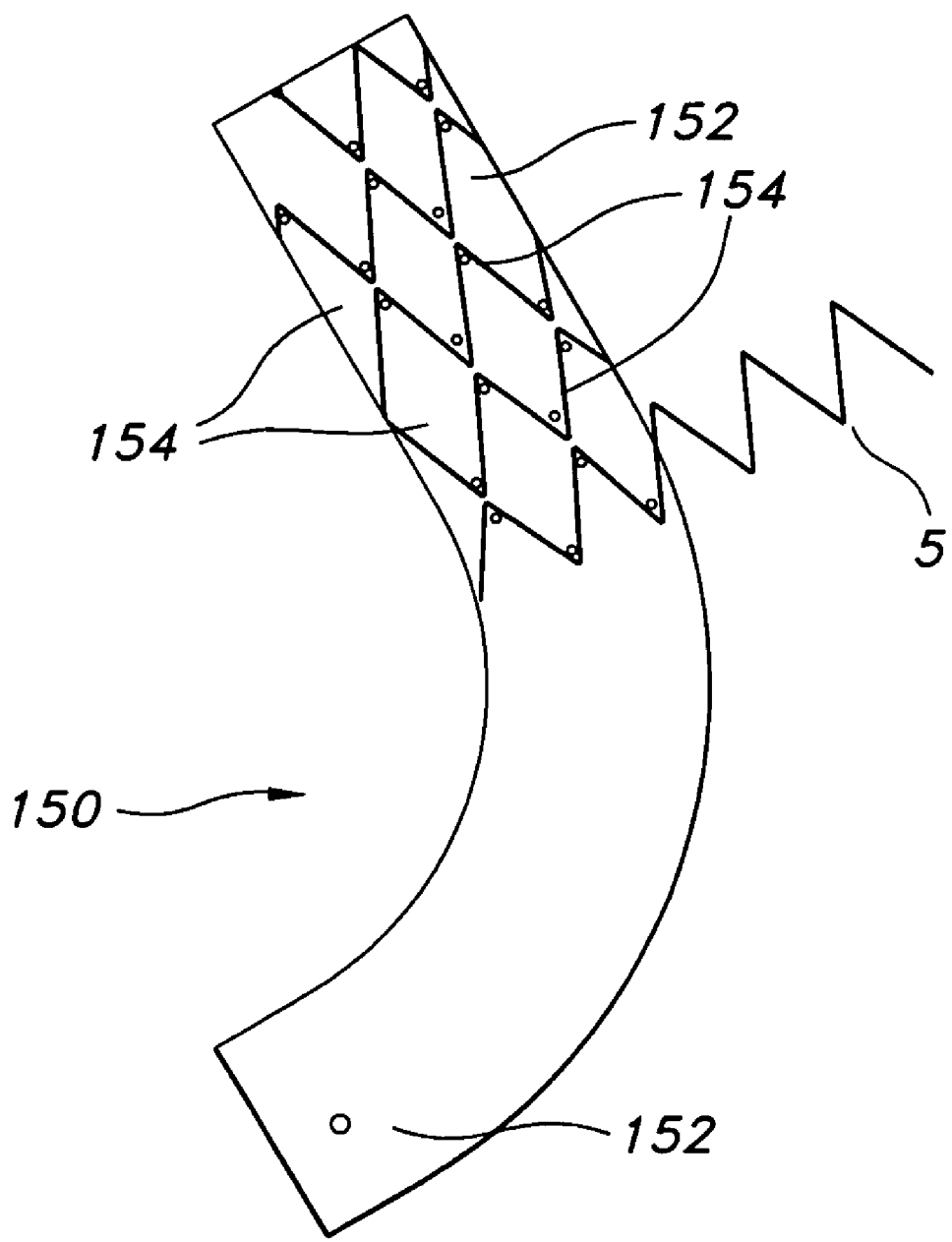
FIG. 21 illustrates a method of forming an anatomically correct endoluminal prosthesis by wrapping wire around a curved mandrel or form.

Fabrication of the anatomically correct stent could include many of the common stent manufacturing methods as are referred to above. In a preferred embodiment, the stent is formed around a curved mandrel 150 as is shown in FIG. 21. In this embodiment, the stent is formed from an undulating shape-memory alloy wire 5 which is wrapped around the mandrel and bent along its length to provide an increased amount of material, and eventual vessel support, per winding around the curved mandrel. A typical wire geometry would be circular cross-section wire with a diameter ranging between 0.23 mm (0.009") to 0.38 mm (0.015"). The wire may be straight or may have pre-formed undulations, as seen in FIG. 2. This wrapping approach for stent fabrication is described in U.S. Pat. No. 5,405,377, which is hereby incorporated by reference.

In the case of the anatomically correct stent, the curved mandrel provides a basis for as equal a distribution as possible of the wire as it is wrapped around the mandrel. In the preferred embodiment, the stent wire is secured at one end with screw 152 and the wire is wrapped around pins 154, which are placed along the body of the mandrel as shown in FIG. 21. The diameter of the mandrel is sized to represent the preferred inner diameter of the deployed stent in situ. Once the wire has been wrapped the desired length of the stent, the final end of the wire is secured to the mandrel by use of screw 156. Wrapping the wire around a curved mandrel allows for an equal distribution of wires and turns along the length of the stent and therefore and equal vessel support force once the stent is deployed in vivo. The wire may, however, be wrapped in such a manner as to provide an unequal distribution of wire as necessary to form the desired curvature or distribution of wire. The curved mandrel may consist of a rigid mandrel shaped into the desired geometry for the final stent configuration or a malleable mandrel that may be selectively shaped and secured or rigidified for fabricating any stent shape of choice. Stainless steel is the generally preferred mandrel metal due to the very stable oxide layer, which forms particularly in response to oven heating during thermal processing.

Figure 22:
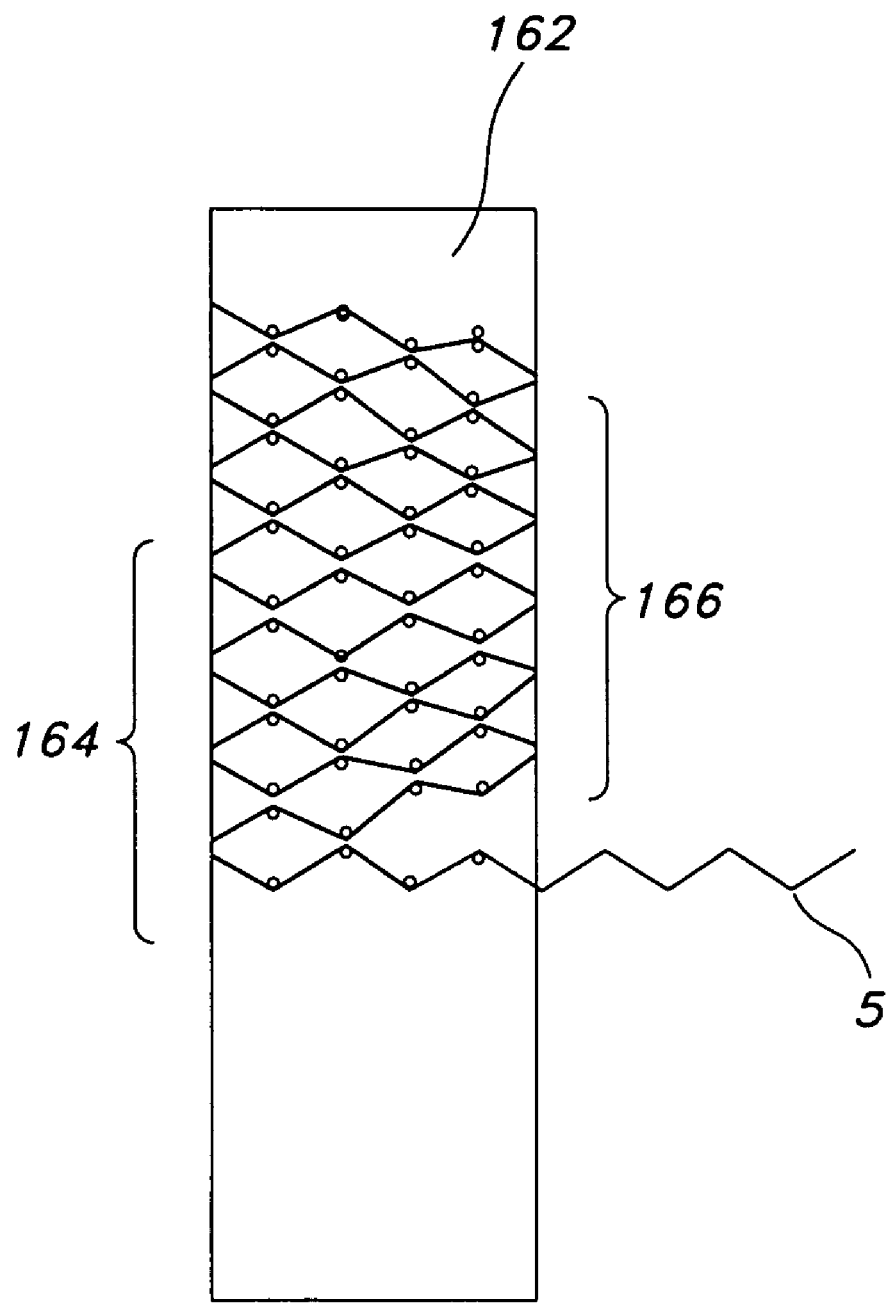
FIG. 22 illustrates a method of forming an anatomically correct endoluminal prosthesis by wrapping wire around a straight mandrel or form in such a way as to bias the pitch of the wrapped wire along the length of the prosthesis to allow for an equal distribution of wire once the prosthesis is formed into its final shape.

Were the stent designed on a straight mandrel, the eventual bending of the stent would result in more material placed on the inside of the curve. In that instance, it is possible to design a curved stent by wire wrapping on a straight mandrel for eventual use as a curved stent. The wire 5 is wrapped on a straight mandrel 162 such that in the area of the eventual stent curvature, variable amounts of wire and in effect, varying cell size is used. Using a larger pitch on one side of the stent and smaller on the other would create an area of curvature. FIG. 22 illustrates the wrapping of a curved stent on a straight mandrel. Areas of less pitch 164 represent the eventual inside of the curve to be fabricated, while areas of increased pitch 166 correspond to the outside of the curve. If a straight mandrel is used, the stent would be heat set on the mandrel. Once the stent is removed from the mandrel it would bend naturally into the curvature imposed by the unequal distribution of wire around the stent. Alternatively, if a reshapable mandrel is used, the stent may be fabricated on the mandrel in a straight form. The system may then be formed into the desired anatomical shape while letting the wrappings slip into the correct positions. This final shaped mandrel and wire system is then heat-treated. In an alternative embodiment, the wire may be wrapped around a mandrel to preset a shape, removed from the mandrel and placed into a mold of the desired shape. The mold and wire would then be heated to set the stent into the desired shape.

Following wrapping of the wire around the mandrel, this wire and mandrel system is heat treated to anneal the wire and set the desired stent shape into position. A typical heat treatment regime anneals the mandrel with a nitinol wire-wound stent scaffold in situ (shape-memory alloy wire was previously wound in cold-worked condition) by heat treating at 500° C. for approximately 25 minutes. The wire-wound mandrel is then dipped in cold water at approximately 2° C. This heat treatment and quenching substantially transforms the wire alloy into its martensite phase, which is malleable and facilitates the removal of the wire scaffold from the mandrel. The wire scaffold is then warmed to 31° C., which allows the shape memory alloy to resume its heat treated shape. The above heat-treatment process does not apply to stainless steel, balloon expandable stents. Nitinol tube stents would be bent in the cold-drawn condition to required curvatures on tube-bending equipment.

Once the wire scaffold is removed from the mandrel, the opposing peaks and valleys of the undulations of the helically wound scaffold are connected in some manner, preferably with a suture as identified in U.S. Pat. No. 5,405,377 and shown in FIG. 1B. The result is a helically wound wire stent with alternating peaks and valleys to provide wall support to the vessel in which it is to be deployed. It should be noted that in the wrapped wire approach to fabrication, as described above, any number of wire patterns are possible. The design of the wrapped stent is not restricted to the use of undulating wire. Specific wire patterns may be used that serve to allow the stent to be constricted during delivery and have the desired dilatation characteristics upon deployment. Stent cells are generally linked V-shapes or quadrilaterals, but may be of any size and shape so as to facilitate stent loading or folding onto a delivery system and stent deployment into a body lumen with the desired dilatation force and flexibility. Stent cells are designed on the basis of their ability to be contracted and closed tightly to result in a minimal increase in the cross-sectional area of the delivery catheter. Stent cells generally remain closed during delivery of the stent. During stent deployment, the cell structures open to approximately the size at which they were fabricated on the mandrel. The angle of the bent, undulating wires of a V-shape cell on wire-wound stents such as those in U.S. Pat. No. 5,405,377 typically covers a range of 30 to 60 degrees. The number of cells disposed around the circumference is best between six to twelve, but may vary depending on the design and intended use of the stent.

It is necessary to provide for anatomically correct stent in a manner that is feasible for use, manufacturing, inventory and marketing. Such requirements preclude creating an inventory of all possible anatomical variations. Even so, while preformed size ranges are the preferred manner to provide for anatomically correct stents, an alternative embodiment would be to provide a method to create these stents on a custom basis. Providing for a custom stent design would require that the stent be manufactured according to specifications provided by the physician. The stent would be fabricated at the company of manufacture or at the hospital. The stent could be manufactured by an automated system that produces the stent with minimal input such as the dimensions, curvature and treatment site. An automated system would be especially convenient at the hospital of use.

In one embodiment, a hospital would have a number of prefabricated straight stents available in varying diameters, yet not heat treated to set in the mechanical properties. As well, a number of molds or mandrels would be on site being sized to various anatomical structures. The molds or mandrels may even be flexible to allow instant adjustment to a unique anatomical measurement. The physician would take the necessary measurements from the body lumen under treatment. From these measurements, a curved mold or mandrel would be selected to best suit the anatomical site. Under sterile conditions, the straight stent would be fitted to the mold or mandrel, either before or after adjustment, and subjected to heat treating and quenching as would normally be performed at a manufacturing plant. The heat treatment would establish the desired shape and mechanical properties for the stent. The stent would then be loaded on a catheter and inserted to the body lumen for treatment. Alternative embodiments for custom-built stents or on-site stent fabrication are possible and the above description should not be interpreted to limit the scope of the invention.

Multiple filaments, multiple materials, designs alternating along the length of the stent, coverings, coatings, anchors or hooks, varying wire cross-section or size, various attachment means such as welding, gluing, crimping or twisting wires and many other conceivable stent fabrication options are conceived of. The cell sections of the stent may be altered along the length of the stent to bias the stent towards a curved shape. It is understood that other features of anatomically correct stents such as multiple curves, apertures, non round segments, bevels, branching, tapering and flaring may be designed into the stent easily by choice of the mandrel design.

As stent fabrication has many conceivable approaches, the fabrication of the anatomically correct stent is not limited or restricted to the examples provided above.

The curved stents would be delivered in a minimally invasive manner to the treatment site using methods and devices that are well known in the art. Preferably, the stent is designed of a material with sufficient elasticity to allow the stent to be compressed to a smaller diameter upon delivery of the stent to the treatment site, yet the stent would recoil, expand and assume its designed curvature upon deployment. Common techniques for delivering so called "self-expanding" stents include delivery of the reduced diameter stent on a catheter being held down by a thin-walled sheath; snaking the system through the body lumens to the treatment site and deployment of the stent at the site by removal of the sheath. Typically, the sheath is removed by pulling back the sheath, however sheath removal may be achieved by tearing the sheath, dissolving the sheath, unwrapping the sheath or in any manner as is commonly practiced in the art.

Deployment of stents, however, is not restricted to self-expanding stents and a sheath covering. In many cases the stent may be fully or partially balloon expandable. Also, the delivery system may include features to allow the stent to be retained at the ends more positively than just with a sheath alone. A common methods used to retain the ends of a stent during delivery include the use of retaining rings over the ends of the stent and beneath the sheath as seen in U.S. Pat. No. 4,950,227, Stent Delivery System, incorporated here by reference. The rings are displaced during stent dilatation and they release the ends of the stent. Another retaining method includes the use of small fibers or whiskers positioned through the cells of the ends of the stent as is shown in U.S. Pat. No. 5,824,058, Prosthesis Delivery incorporated here by reference. The delivery system may be adapted to fit the stent as is shown in U.S. Pat. No. 5,484,444, device for the Implantation of Self-Expanded Endoprosthesis, incorporated herein by reference. The delivery system may further include coatings and specific designs to hold the stent in a secure position, such as grooves in the catheter or balloon, partial coverings of the ends of the stent or the addition of soft or sticky materials and filaments or sutures to tie down the stent or delivery system. The curved stent delivery system is not meant to be restricted or limited to the examples provided as many more designs are conceived of or known in the art.

The delivery system for an anatomically correct stent and in particular a curved stent must be designed to prevent curvature of the stent delivery system prior to stent deployment. For purposes of delivery of the stent to the correct location in the body, the delivery system, which is preferably a catheter, should maintain an axial straight configuration when placed into a straight lumen or vessel. The preferred embodiment, however, has enough flexibility to bend through curved or tortuous vessels and lumens while transversing them without adversely affecting the anatomy.

Upon positioning of the stent, yet prior to deployment, the catheter may be allowed or induced to assume the approximate anatomical curvature or shape into which the anatomically correct stent is to be deployed. In a preferred embodiment, the catheter shaft would be sufficiently firm enough to support the stent during delivery and to allow pushing and torquing of the system with good response. However, during stent delivery and then catheter removal, the delivery system would be soft enough so as not to adversely affect the anatomy, the stent or the positioning of the stent. The exact balance of firmness to softness may be found by any of the means as known in the art, including, but not limited to, a catheter made of a polymer material tailored to the correct specifications; a catheter shaft having two or more materials either layered or transitioned axial; a catheter shaft of two or more different materials of varying durometers; a catheter shaft supported by a removable stiffening rod or material or a catheter shaft reinforced with braiding or the like at specific sites along its axis. In one embodiment, the catheter shaft may be designed to follow a similar curvature as presented in the anatomy and the anatomically correct stent. The curvature may be maintained in a straighter position by a stiffening wire or sheath during stent delivery.

The orientation of the stent and in particular, the location of the angle of the stent while on the delivery catheter may be controlled by a visual or tactile indicator built into the delivery system handle. The stent design may be indicated on the handle along with the defining geometries as were indicated by the stent code number. A preferred method of placing this information on the catheter handle is by molding it into the handle. As well, color coding the delivery system or parts of the system including the code numbers or handle indicator would make stent identification and orientation much easier. Symbols on the delivery system such as arrows may help to identify the stent orientation. Accurate delivery system angular orientation may be achieved by any of the commonly used methods in the art including designing the system to be highly responsive to torque by material selections for the catheter and using braided wall structures.

The delivery system in this invention will have to guarantee an accurate angular positioning with respect to the torque being applied to the catheter handle. Multiple coaxial components such as a sheath and the underlying catheter will want to slip from one another around the rotational axis yet may be kept in unified angular position by use of interlocking geometries, such as a square handle shaft over which the proximal portion of the sheath is square and thus prohibited from angular rotation with respect to the catheter shaft. Many solutions exist in the art to maintain the respective positions of the delivery system components and the stent during stent delivery.

The delivery system preferably has visible markers to allow the user to align the ends of the stent with a chosen location on the catheter and thus allow the user to see both the stent position and catheter position. In many cases a delivery catheter is designed to allow partial deployment of the stent, visualization of the deployment and recapturing and repositioning of the stent in the vessel as necessary. In the case of the curved stent it is desirable that this repositioning method and the catheter design therein be adaptable for stent rotation, or angular orientation as well as axial positioning within the vessel. Such rotational, or angular orientation would require sufficient force between the stent, the catheter and the sheath to be effective. Sufficient force between the stent and delivery system may be possible by requiring that a portion of the stent be detained within the sheath or recaptured to allow the forces of contact with the stent to overcome the forces developed while torquing the exposed portion of the stent against the vessel wall. The stent is preferably fully covered during positioning or repositioning to prevent injury of the vessel wall. Recovering of the semi-deployed stent is enabled by any of the methods as described above and in particular by holding the most distal end of the stent secure on the delivery system until full deployment is desired.

While there have been described what are presently believed to be the preferred embodiment of the invention, those skilled in the art will realize that various changes and modifications may be made to the invention without departing from the spirit of the invention, and it is intended to claim all such changes and modifications as fall within the scope of the invention.

What is claimed is:

1. An endoluminal prosthesis comprising:
a proximal end, a distal end and a hollow tubular body having a central longitudinal axis, the body comprising a stent scaffold of helically wound undulating wires having alternating peaks and valleys to define turns thereat;
the hollow tubular body comprising at least one segment of curvature along a portion of a longitudinal length of the body, wherein the central longitudinal axis of the body is curved along said portion of the longitudinal length of the body throughout the segment of curvature;
the segment of curvature comprising an inside of the curvature and an outside of the curvature;
wherein the wires and their turns are distributed substantially equally and uniformly displaced along the length of the prosthesis, including being distributed substantially equally and uniformly displaced along the length of the segment of curvature, to provide a constant pitch of the wires therealong.

2. An endoluminal prosthesis comprising:
a proximal end, a distal end and a hollow tubular body having a central longitudinal axis, the body comprising a stent scaffold having V-shaped or quadrilateral-shaped cells, the stent scaffold consisting essentially of helically wound undulating wires having alternating peaks and valleys to define turns thereat;
the hollow tubular body comprising at least one segment of curvature along a portion of a longitudinal length of the body, wherein the central longitudinal axis of the body is curved along said portion of the longitudinal length of the body throughout the segment of curvature;
the segment of curvature comprising an inside of the curvature and an outside of the curvature;
wherein the wires and their turns are distributed substantially equally and uniformly displaced along the length of the prosthesis, including being distributed substantially equally and uniformly displaced along the length of the segment of curvature, to provide a constant pitch of the wires therealong.

3. The prosthesis of claim 2 wherein the segment of curvature is curved in at least one plane with respect to the central axis of the body.

4. The prosthesis of claim 2 wherein the segment of curvature is curved in at least two planes with respect to the central axis of the body.

5. The prosthesis of claim 2 wherein the hollow tubular body has at least two segments of curvature wherein the segments of curvature are located in successive progression along the body of the prosthesis and the segments are curved within the same plane of curvature.

6. The prosthesis of claim 2 wherein hollow tubular body has at least two segments of curvature wherein the segments of curvature are located in successive progression along the body of the prosthesis and the segments are curved within different planes of curvature.

7. The prosthesis of claim 2 wherein the hollow tubular body has at least two segments of curvature wherein the segments of curvature overlap at least a portion of one another and the segments of curvature are curved within different planes of curvature.

8. The prosthesis of claim 2 comprising both segments of curvature which overlap and segments of curvature which do not overlap.

9. The prosthesis of claim 2 wherein the prosthesis comprises at least one segment of curvature to approximate an anatomical shape.

10. The prosthesis of claim 9 wherein the prosthesis approximates the anatomical shape of the anatomical site intended for placement of the prosthesis.

11. The prosthesis of claim 2 wherein the wires comprise a shape memory alloy.

12. The prosthesis of claim 2 wherein the wires comprise a super elastic alloy.

13. The prosthesis of claim 2 wherein the wires comprise a polymer.

14. The prosthesis of claim 2 wherein the wires are nitinol.

15. The prosthesis of claim 2 wherein the peaks of adjacent undulating wires are interconnected.

16. The prosthesis of claim 2 wherein the hollow tubular body comprises a thin-walled tube material wherein the center of the thin-walled tube provides the center of the prosthesis.

17. The prosthesis of claim 2 wherein the prosthesis further comprises at least one taper along the length of the body.

18. The prosthesis of claim 2 wherein the prosthesis further comprises at least one aperture on the body between the proximal end and the distal end.

19. The prosthesis of claim 2 wherein the prosthesis further comprises at least one non-circular cross-section along the length of the body.

20. The prosthesis of claim 2 wherein the prosthesis further comprises at least one branch of the prosthesis that extends away from the body of the prosthesis.

21. The prosthesis of claim 2 wherein at least a portion of the prosthesis is covered with a graft covering.

22. The prosthesis of claim 2 wherein the wires have an increased pitch at the outside segment and have a reduced pitch at the inside segment when disposed on a straight mandrel.

23. The prosthesis of claim 22 wherein the increased pitch at the outside segment is relative to the reduced pitch at the inside segment.

24. An endoluminal prosthesis comprising:
a proximal end, a distal end and a hollow tubular body having a central longitudinal axis, the body comprising a stent scaffold having V-shaped or quadrilateral-shaped cells consisting essentially of helically wound undulating wires having alternating peaks and valleys to define turns thereat;
the hollow tubular body comprising at least one segment of curvature along a portion of a longitudinal length of the body, wherein the central longitudinal axis of the body is curved along said portion of the longitudinal length of the body throughout the segment of curvature;
the segment of curvature comprising an inside of the curvature and an outside of the curvature;
wherein the wires and their turns are distributed substantially equally and uniformly displaced along the length of the prosthesis, including being distributed substantially equally and uniformly displaced along the length of the segment of curvature;
wherein the wires have an increased pitch at the outside segment and have a reduced pitch at the inside segment when disposed on a straight mandrel;
and further wherein the hollow tubular body is geometrically shaped and sized to approximate an anatomical shape.

25. The prosthesis of claim 24 wherein the prosthesis approximates the anatomical shape of the anatomical site intended for placement of the prosthesis.

26. The prosthesis of claim 24 wherein the wires comprise a shape-memory alloy.

27. The prosthesis of claim 24 wherein the wires comprise a super elastic alloy.

28. The prosthesis of claim 24 wherein the wires comprise a polymer.

29. The prosthesis of claim 24 wherein the wires are nitinol.

30. The prosthesis of claim 24 wherein the peaks of adjacent undulating wires are interconnected.

31. The prosthesis of claim 24 wherein the hollow tubular body comprises a thin-walled tube material wherein the center of the thin-walled tube provides the center of the prosthesis.

32. The prosthesis of claim 24 wherein the prosthesis further comprises at least one taper along the length of the body.

33. The prosthesis of claim 24 wherein the prosthesis further comprises at least one aperture on the body between the proximal end and the distal end.

34. The prosthesis of claim 24 wherein the prosthesis further comprises at least one non-circular cross-section along the length of the body.

35. The prosthesis of claim 24 wherein the prosthesis further comprises at least one branch of the prosthesis that extends away from the body of the prosthesis.

36. The prosthesis of claim 24 wherein the increased pitch at the outside segment is relative to the reduced pitch at the inside segment.

37. The prosthesis of claim 24 wherein the wires and their turns have a constant pitch along the length of the segment of curvature.

* * * * *